United States Patent
Holland et al.

(10) Patent No.: US 8,871,793 B2
(45) Date of Patent: Oct. 28, 2014

(54) METAXALONE COCRYSTALS

(75) Inventors: Joanne Holland, Histon (GB);
Christopher Frampton, Suffolk (GB);
Alan Chorlton, Newmarket (GB);
Daniel Gooding, Cambridge (GB)

(73) Assignee: Nuformix Limited (GB)

( * ) Notice: Subject to any disclaimer, the term of this patent is extended or adjusted under 35 U.S.C. 154(b) by 184 days.

(21) Appl. No.: 13/518,177

(22) PCT Filed: Dec. 22, 2010

(86) PCT No.: PCT/IB2010/003460
§ 371 (c)(1),
(2), (4) Date: Mar. 7, 2013

(87) PCT Pub. No.: WO2011/077252
PCT Pub. Date: Jun. 30, 2011

(65) Prior Publication Data
US 2013/0158083 A1    Jun. 20, 2013

Related U.S. Application Data

(60) Provisional application No. 61/289,766, filed on Dec. 23, 2009, provisional application No. 61/381,244, filed on Sep. 9, 2010.

(51) Int. Cl.
*A61K 31/421* (2006.01)
*C07D 263/24* (2006.01)
*C07C 55/10* (2006.01)
*C07C 65/10* (2006.01)
*C07C 57/145* (2006.01)
*C07C 57/15* (2006.01)
*C07C 55/14* (2006.01)

(52) U.S. Cl.
CPC .............. *C07D 263/24* (2013.01); *C07C 65/10* (2013.01); *C07C 57/15* (2013.01); *C07C 55/10* (2013.01); *C07C 57/145* (2013.01); *C07C 55/14* (2013.01); *A61K 31/421* (2013.01)
USPC .......................................... 514/376; 548/232

(58) Field of Classification Search
CPC .... A61K 31/421; C07D 263/24; C07C 55/10; C07C 57/145; C07C 57/15; C07C 65/10
See application file for complete search history.

(56) References Cited

U.S. PATENT DOCUMENTS

| | | |
|---|---|---|
| 2005/0181041 A1 | 8/2005 | Goldman |
| 2007/0059356 A1 | 3/2007 | Almarsson et al. |

FOREIGN PATENT DOCUMENTS

| | | |
|---|---|---|
| WO | 2004/019937 A1 | 3/2004 |
| WO | 2005/055983 A2 | 6/2005 |
| WO | 2008/045473 A1 | 4/2008 |
| WO | 2011/077252 A2 | 6/2011 |

OTHER PUBLICATIONS

International Search Report and Written Opinion dated Jun. 28, 2011 of PCT International Application No. PCT/IB2010/003460.
Shan et al., "The role of cocrystals in pharmaceutical science", Drug Discovery Today, vol. 13, No. 9-10, May 1, 2008, pp. 440-446.

*Primary Examiner* — Kamal Saeed
(74) *Attorney, Agent, or Firm* — J.A. Lindeman & Co., PLLC

(57) ABSTRACT

The invention relates to improvements of the physiochemical and/or the pharmaceutical properties of metaxalone. Disclosed herein are several new cocrystals of metaxalone, including: a 1:1 metaxalone adipic acid cocrystal, a 1:0.5 metaxalone fumaric acid cocrystal, a 1:1 metaxalone salicylic acid cocrystal, a 1:0.5 metaxalone succinic acid cocrystal, and a 1:0.5 metaxalone maleic acid cocrystal. The therapeutic uses of these metaxalone cocrystals are described as well as therapeutic compositions containing them.

24 Claims, 32 Drawing Sheets

Fig. 3: TGA Trace for 1:1 Metaxalone Adipic Acid Cocrystal

Fig. 4: ¹H NMR Spectrum of 1:1 Metaxalone Adipic Acid Cocrystal

Fig. 5: XRPD Pattern for 1:0.5 Metaxalone Fumaric Acid Cocrystal

Fig. 6: ORTEP Drawing of 1:0.5 Metaxalone Fumaric Acid Cocrystal

Fig. 7: Packing diagram of 1:0.5 Metaxalone Fumaric Acid Cocrystal

Fig. 8: Calculated XRPD Pattern for 1:0.5 Metaxalone Fumaric Acid Cocrystal

Fig. 9: DSC Trace for 1:0.5 Metaxalone Fumaric Acid Cocrystal

Fig. 10: TGA Trace for 1:0.5 Metaxalone Fumaric Acid Cocrystal

Fig. 11: ¹H NMR Spectrum of 1:0.5 Metaxalone Fumaric Acid Cocrystal

Fig.12: XRPD Pattern for 1:1 Metaxalone Salicylic Acid Cocrystal

Fig. 13: ORTEP Drawing of 1:1 Metaxalone Salicylic Acid Cocrystal

Fig. 14 Packing Diagram of 1:1 Metaxalone Salicylic Acid Cocrystal

Fig. 15: Calculated XRPD Pattern for 1:1 Metaxalone Salicylic Acid Cocrystal

Fig. 17: TGA Trace for 1:1 Metaxalone Salicylic Acid Cocrystal

Fig. 18: ¹H NMR Spectrum of 1:1 Metaxalone Salicylic Acid Cocrystal

Fig. 20: ORTEP Drawing of 1:0.5 Metaxalone Succinic Acid Cocrystal

Fig. 21: Packing Diagram of 1:0.5 Metaxalone Succinic Acid Cocrystal

Fig.22: Calculated XRPD Pattern for 1:0.5 Metaxalone Succinic Acid Cocrystal

Fig. 23: DSC Trace for 1:0.5 Metaxalone Succinic Acid Cocrystal

Fig. 24: TGA Trace for 1:0.5 Metaxalone Succinic Acid Cocrystal

Fig. 25: ¹H NMR Spectrum of 1:0.5 Metaxalone Succinic Acid Cocrystal

Fig. 27: ORTEP Drawing of 1:0.5 Metaxalone Maleic Acid Cocrystal

Fig. 28: Calculated XRPD Pattern for 1:0.5 Metaxalone Maleic Acid Cocrystal

Fig. 31: ¹H NMR Spectrum of 1:0.5 Metaxalone Maleic Acid Cocrystal

METAXALONE COCRYSTALS

CROSS-REFERENCE TO RELATED APPLICATIONS

This application claims priority to PCT International Application No. PCT/IB2010/003460 filed 22 Dec. 2010; which claims priority to U.S. provisional application 61/289,766, filed 23 Dec. 2009, and to U.S. provisional application 61/381,244, filed 9 Sep. 2010. The disclosure of both provisional applications is incorporated herein by reference.

FIELD OF THE INVENTION

The invention relates to new crystalline compounds containing metaxalone, more particularly, the invention relates to metaxalone cocrystals, therapeutic uses of those metaxalone cocrystals, and pharmaceutical compositions containing them.

BACKGROUND

Metaxalone, 5-[(3,5-dimethylphenoxy)methyl]-2-oxazolidinone, shown below, is a musclerelaxant used to relax muscles and relieve pain caused by strains, sprains, and other musculoskeletal conditions, particularly muscle spasms and back pain.

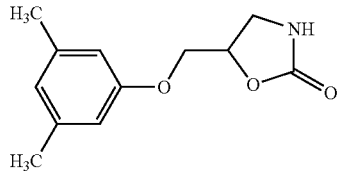 [SMILES: Cc1cc(C)cc(OCC2CNC(=O)O2)c1]

Metaxalone is a white to almost white, odourless crystalline powder freely soluble in chloroform, soluble in methanol and in 96% ethanol but practically insoluble in water. Metaxalone melts, without decomposition, at 121.5-123° C. Metaxalone is further described at Monograph no. 5838 of the Merck Index (Eleventh Addition, Merck & Co., 1989) and is also identified by CAS Registry Number: 1665-48-1. Preparation of metaxalone is described in Lunsford et al., J. Am. Chem. Soc. 82, 1166 (1960) and U.S. Pat. No. 3,062,827.

Metaxalone is marketed in 800 mg tablets under the SKELAXIN® tradename. As an interneuronal blocking agent, metaxalone acts on the central nervous systems (CNS) to produce muscle relaxant effects, and is used as an adjunct to rest, physical therapy, and other measures for the relief of discomforts associated with painful musculoskeletal conditions. Metaxalone is used to treat acute, painful muscle spasms. The mechanism of action of metaxalone in humans has not been established but may be due to general central nervous system depression. Metaxalone has no direct action on the contractile mechanism of striated muscle, the motor end plate, or the nerve fiber. The bioavailability of metaxalone is significantly improved when it is taken with food. Specifically, in one study, compared to fasted conditions, the presence of food at the time of drug administration increased C(max) by 177.5% and increased AUC(last) by 123.5% and AUC(inf) by 115.4%. Based on the information in the SKELAXIN® product data sheet, patients receiving metaxalone therapy are informed that, due to a food effect, taking metaxalone with food may result in an increase in the oral bioavailability of metaxalone compared to taking metaxalone without food. See SKELAXIN® Product Data Sheet, April 2008; U.S. Pat. Nos. 6,407,128; and 6,683,102; and http://en.wikipedia.org/wiki/Metaxalone, Dec. 6, 2009. This food effect may effect dosing for a particular patient. In view of the food effect on metaxalone bioavailabity, the currently developed formulations of metaxalone do not achieve the goal of a sufficiently bioavailable form of metaxalone.

Active pharmaceutical ingredients (API's) which, like metaxalone, are generally less water soluble and less bioavailable create huge problems for the pharmaceutical industry. Research has shown that some drug candidates fail in the clinical phase due to poor human bioavailability and problems with the formulation. Traditional methods to address these problems, without completely redesigning the molecule, include salt selection, producing amorphous material, particle size reduction, pro-drugs, and different formulation approaches. Some attempts to use such techniques with metaxalone are described, for example, in WO 2004/019937 A1, WO 2005/016310 A1, WO 2007/079189 A2, and WO 2009/19662 A2.

Although therapeutic efficacy is the primary concern for an API, the salt and solid state form (i.e., the crystalline or amorphous form) of a drug candidate can be critical to its pharmacological properties and to its development as a viable API. Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate solid state form for further drug development can reduce the time and the cost of that development.

Obtaining crystalline forms of an API is extremely useful in drug development. It permits better characterization of the drug candidate's chemical and physical properties. It is also possible to achieve desired properties of a particular API by forming a cocrystal of the API and a coformer. Crystalline forms often have better chemical and physical properties than the free base in its amorphous state. Such crystalline forms may, as with the cocrystals of the invention, possess more favorable pharmaceutical and pharmacological properties or be easier to process than known forms of the API itself. For example, a cocrystal may have different dissolution and solubility properties than the API itself and can be used to deliver APIs therapeutically. New drug formulations comprising cocrystals of a given API may have superior properties over its existing drug formulations. They may also have better storage stability.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

A cocrystal of an API is a distinct chemical composition of the API and coformer and generally possesses distinct crystallographic and spectroscopic properties when compared to those of the API and coformer individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC).

SUMMARY

The invention relates to new cocrystals of metaxalone, which have improved physiochemical and/or pharmaceutical properties over metaxalone itself. The invention also relates to therapeutic compositions containing cocrystals of metaxalone as well as methods of treating muscle pain with cocrystals of metaxalone.

DETAILED DESCRIPTION

Figure 1:
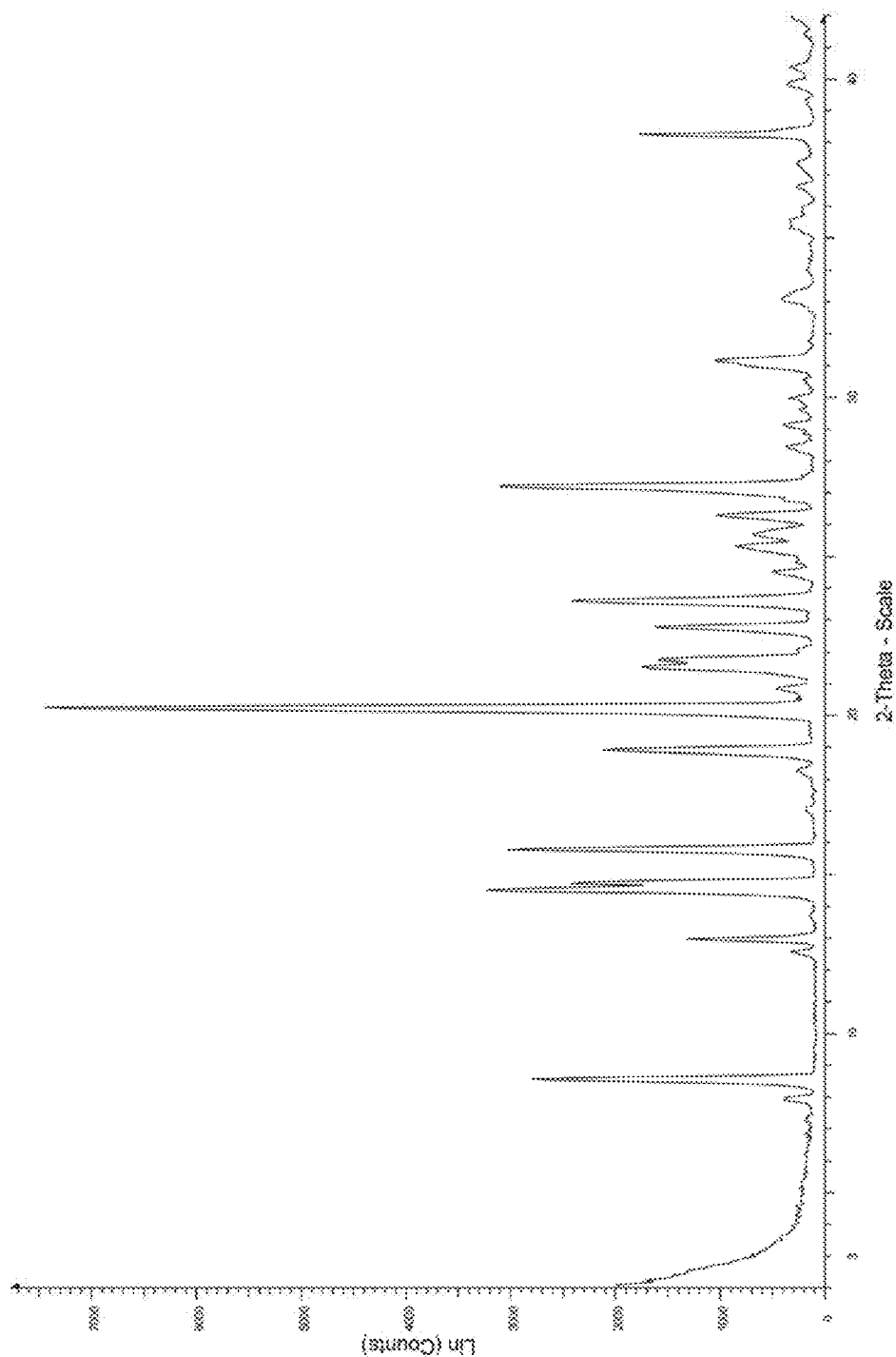
FIG. 1 shows an XRPD pattern for the 1:1 metaxalone adipic acid cocrystal.

The invention relates to improvements of the physiochemical and/or the pharmaceutical properties of metaxalone. Disclosed herein are several new cocrystals of metaxalone, including: a 1:1 metaxalone adipic acid cocrystal, a 1:0.5 metaxalone fumaric acid cocrystal, a 1:1 metaxalone salicylic acid cocrystal, a 1:0.5 metaxalone succinic acid cocrystal, and a 1:0.5 metaxalone maleic acid cocrystal. Each cocrystal represents a new composition of matter. The therapeutic uses of these metaxalone cocrystals are described as well as therapeutic compositions containing them. The cocrystals and the methods used to characterize them are described below.

Therapeutic Uses of the Metaxalone Cocrystals

The invention further relates to the therapeutic use of at least one metaxalone cocrystal of the invention to treat musculoskeletal disorders, e.g. to relax muscles and relieve pain caused by strains, sprains, and other musculoskeletal conditions, and particularly to treat muscle spasms and back pain. Accordingly, the invention relates to method of treating a musculoskeletal disorder comprising the step of administering to a patient in need thereof a therapeutically effective amount of at least one metaxalone cocrystal of the invention or of a pharmaceutical composition containing at least one metaxalone cocrystal.

The term "treatment" or "treating" means any treatment of a condition or disorder in a mammal, including: preventing or protecting against the condition or disorder, that is, causing the clinical symptoms not to develop; inhibiting the condition or disorder, that is, arresting or suppressing the development of clinical symptoms; and/or relieving the condition or disorder (including the relief of pain associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the condition or disorder. The term "protection" is meant to include "prophylaxis."

Pharmaceutical Compositions Containing Metaxalone Cocrystals

The invention also relates to pharmaceutical compositions comprising a therapeutically effective amount of at least one metaxalone cocrystal according to the invention and a pharmaceutically acceptable carrier (also known as a pharmaceutically acceptable excipient). As mentioned above, these pharmaceutical compositions are therapeutically useful for the treatment of musculoskeletal conditions.

A pharmaceutical composition of the invention may be in any pharmaceutical form which contains at least one metaxalone cocrystal according to the invention. The pharmaceutical composition may be, for example, a tablet, capsule, liquid suspension, injectable, topical, or transdermal. The pharmaceutical compositions generally contain, for example, about 1% to about 99% by weight of at least one metaxalone cocrystal of the invention and, for example, 99% to 1% by weight of at least one suitable pharmaceutical excipient. In one embodiment, the composition may be between about 5% and about 75% by weight of at least one metaxalone cocrystal of the invention with the rest being at least one suitable pharmaceutical excipient or at least one other adjuvant, as discussed below.

A "therapeutically effective amount of at least one metaxalone cocrystal" according to the invention is that which correlates to a therapeutically effective dose of metaxalone itself, generally from about 50 to about 800 mg of metaxalone, preferably about 200 mg to 800 mg. The actual amount required for treatment of any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of metaxalone; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having at least one metaxalone cocrystal of the invention, a carrier should be chosen that maintains the crystalline form. In other words, the carrier should not substantially alter the metaxalone cocrystal. Nor should the carrier be otherwise incompatible with the metaxalone cocrystal used, such as by producing any undesirable biological effect or otherwise interacting in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, at least one metaxalone cocrystal may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing at least one metaxalone cocrystal according to the present disclosure with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Because the metaxalone cocrystal is maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). The metaxalone cocrystals according to the invention may also be used as precursors in the formulation of liquid pharmaceutical compositions. Administration of the metaxalone cocrystals in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the musculoskeletal condition to be treated.

EXAMPLES

The following analytical methods were used to characterize the metaxalone cocrystals of the invention:

X-Ray Powder Diffraction:

X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 2° to 42° 2θ using a step size of 0.05° 2θ and a step time of 0.5 seconds. Samples run under ambient conditions were prepared as flat plate specimens using powder as received without grinding. Approximately, 35 mg of the sample was gently picked into a cavity cut into polished, zero background (510) silicon wafer. All samples were analysed using Diffrac Plus EVA v11.0.0.2 or v13.0.0.2.

Single Crystal X-Ray Diffraction (SCXRD):

Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning Calorimetry (DSC):

DSC data was collected on a TA instruments Q2000 equipped with a 50 position autosampler. The calibration for thermal capacity was carried out using sapphire and the calibration for the energy and temperature was carried out using certified indium. Typically 0.8-1.2 mg of each sample, in a pin-holed aluminium pan, was heated at 10° C./min from 25° C. to 350° C. A purge of dry nitrogen at 50 ml/min was maintained over the sample. The instrument control software was Advantage for Q series v2.8.0.392 and Thermal Advantage v4.8.3. All data analysis was performed using Universal Analysis v4.3A software.

Thermo-Gravimetric Analysis (TGA):

TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C./min from ambient temperature to 350° C. A nitrogen purge at 60 ml/min was maintained over the sample. The instrument control software was Advantage for Q Series v2.8.0.392 and Thermal Advantage v4.8.3

Solution Proton NMR:

$^1$H-NMR spectra were recorded on a Bruker 400 MHz spectrometer equipped with an auto-sampler and controlled by a DRX400 console. The samples Were dissolved in DMSO for analysis. The data was acquired using ICON-NMR v4.0.4 (build 1) running with Topspin v1.3 (patch level 8) using the standard Bruker loaded experiments.

Example 1

1:1 Metaxalone Adipic Acid Cocrystal 1.1 Preparation of 1:1 Metaxalone Adipic Acid Cocrystal Metaxalone (500 mg) and adipic acid (330 mg) were weighed into a glass vial. Isopropyl alcohol (IPA, 1.67 ml) was added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour. An additional 100 µl of IPA was added to filter and the product left to dry under ambient conditions overnight.

1.2 XRPD Characterization of 1:1 Metaxalone Adipic Acid Cocrystal

The experimental XRPD pattern of the 1:1 metaxalone adipic acid cocrystal is shown in FIG. 1. Table 1 lists the angles, °2θ±0.2°2θ, d-spacing, and intensity of the peaks identified in the XRPD pattern of FIG. 1. The entire list of peaks, or a subset thereof, may be sufficient to characterize the cocrystal. One subset of peaks from FIG. 1 that, individually or in combination, may be used to characterize the 1:1 metaxalone adipic acid cocrystal includes 8.5, 15.8, 18.9, 20.2, and 23.6 °2θ±0.2°2θ. The 1:1 metaxalone adipic acid cocrystal may be characterized by a subset of at least three of these peaks.

TABLE 1

| Angle °2θ ± 0.2° 2θ | d value Angstrom | Intensity % |
|---|---|---|
| 7.9 | 11.17 | 5.10 |
| 8.5 | 10.37 | 37.60 |
| 12.5 | 7.06 | 4.20 |
| 12.9 | 6.84 | 17.50 |
| 14.5 | 6.11 | 43.30 |
| 14.7 | 6.02 | 32.60 |
| 15.8 | 5.61 | 40.50 |
| 18.9 | 4.69 | 28.40 |
| 20.2 | 4.39 | 100.00 |
| 20.9 | 4.26 | 6.10 |
| 21.5 | 4.12 | 23.30 |
| 21.8 | 4.08 | 21.30 |
| 22.8 | 3.90 | 21.50 |
| 23.6 | 3.77 | 32.30 |
| 24.5 | 3.63 | 6.40 |
| 25.3 | 3.51 | 11.20 |
| 25.7 | 3.46 | 9.00 |
| 26.3 | 3.39 | 13.70 |
| 27.2 | 3.27 | 41.50 |
| 31.3 | 2.87 | 14.00 |
| 33.1 | 2.70 | 5.40 |
| 38.2 | 2.35 | 23.70 |

1.3 DSC of 1:1 Metaxalone Adipic Acid Cocrystal

Figure 2:
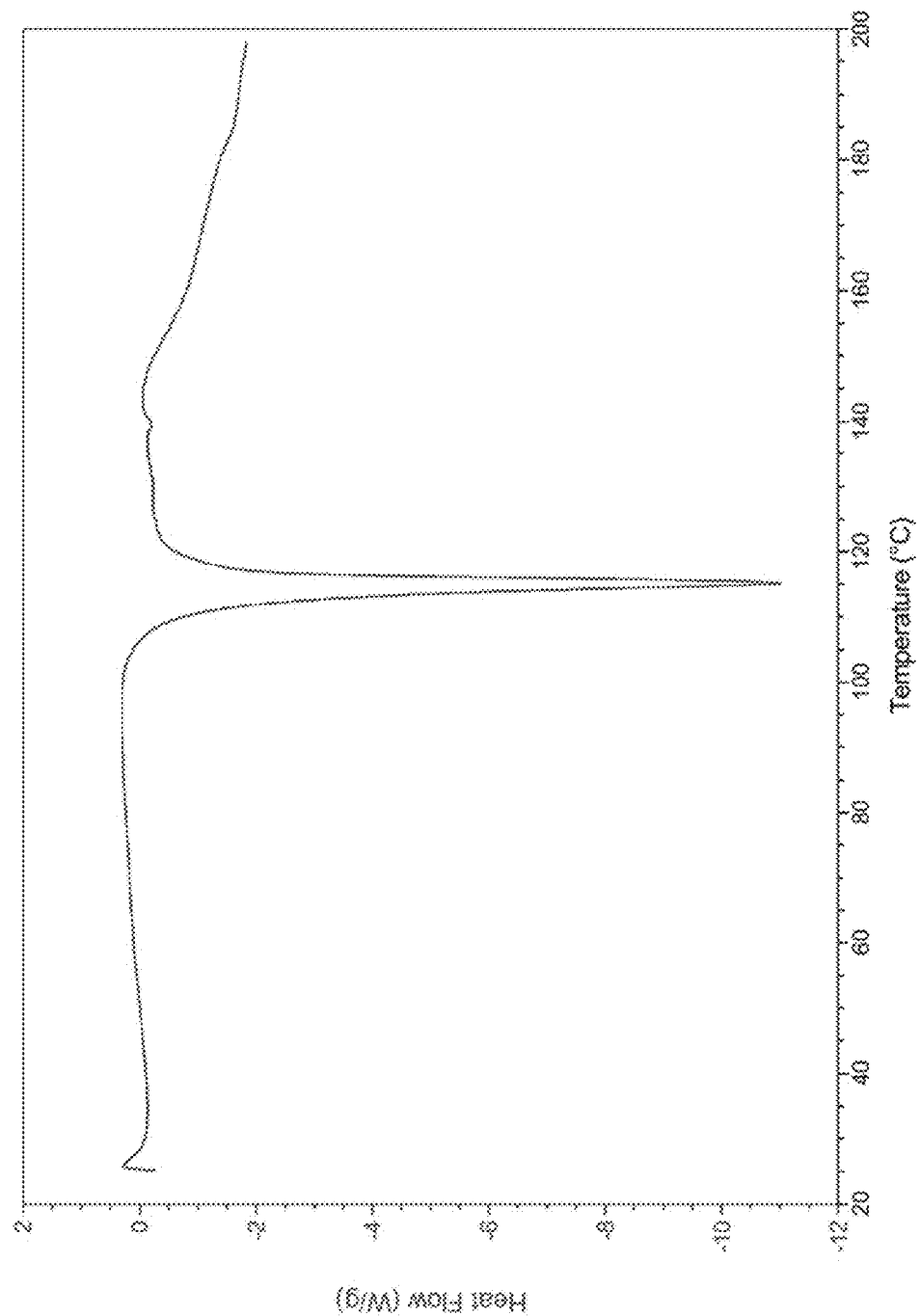
FIG. 2 shows a DSC trace for the 1:1 metaxalone adipic acid cocrystal.

The differential scanning calorimetry (DSC) trace, FIG. 2, shows a melting endotherm with an onset temperature of 112.54° C. and a peak maximum of 115.15° C.

1.4 TGA of 1:1 Metaxalone Adipic Acid Cocrystal

Figure 3:
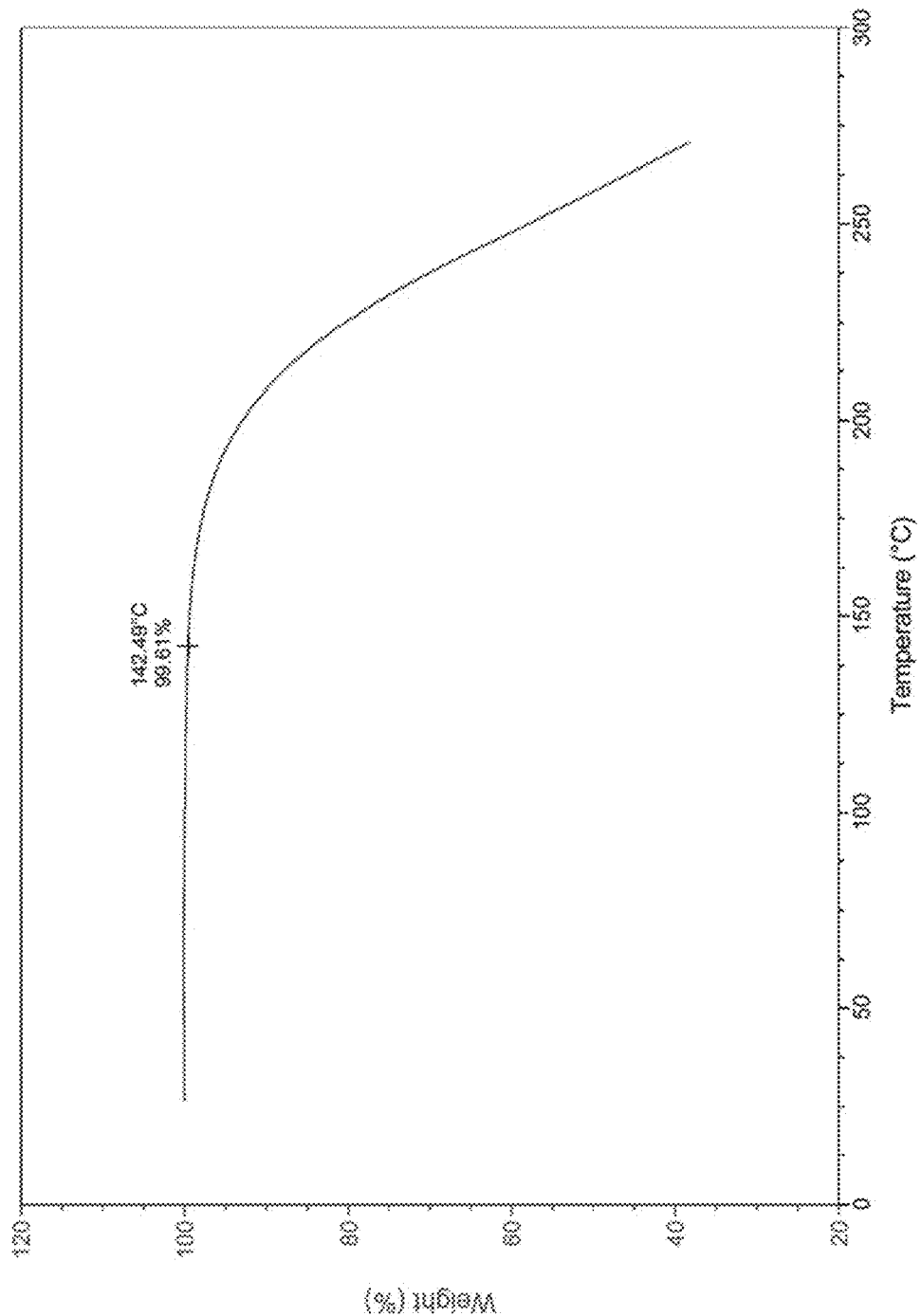
FIG. 3 shows a TGA trace for the 1:1 metaxalone adipic acid cocrystal.

The thermal gravimetric analysis (TGA) trace, FIG. 3, shows no significant weight loss prior to degradation with 99.61% weight remaining at 142.49° C.

1.5 $^1$H NMR of 1:1 Metaxalone Adipic Acid Cocrystal

Figure 4:
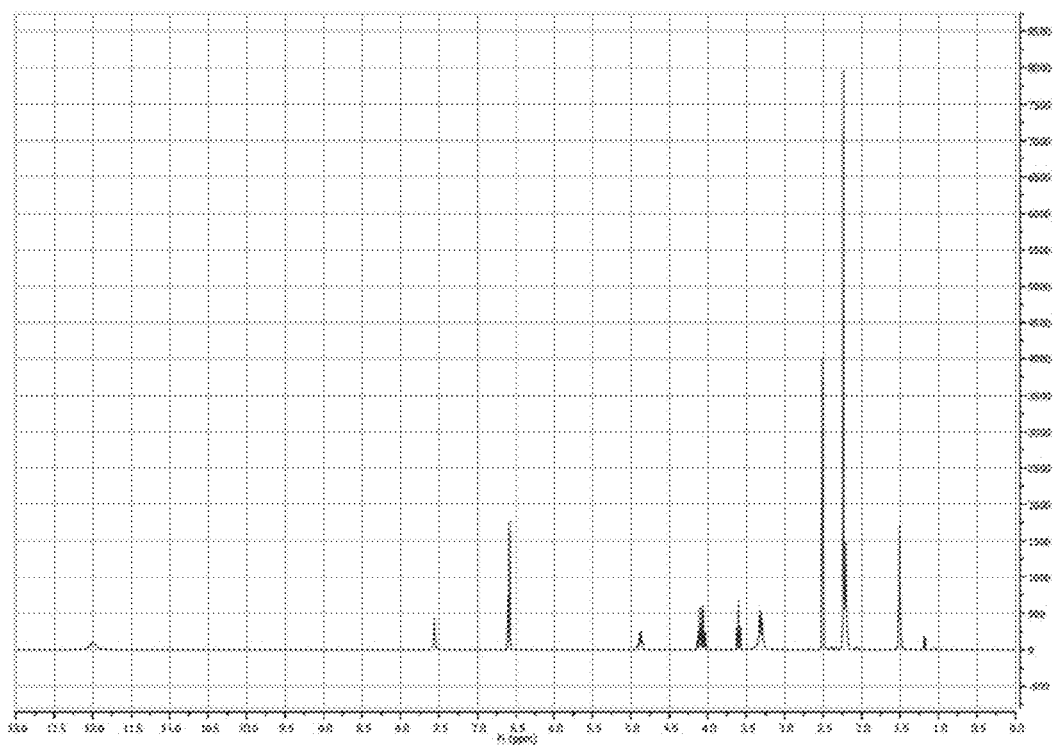
FIG. 4 shows the $^1$H NMR spectrum of 1:1 metaxalone adipic acid cocrystal.

The NMR spectrum of the metaxalone adipic acid cocrystal, shown in FIG. 4, displays the following peaks: $^1$H NMR (400 MHz, d6-DMSO) δ: 12.00 (2H), 7.56 (1H), 6.59 (3H), 4.87 (1H), 4.08 (2H), 3.60 (1H), 3.31 (1H), 2.21-2.23 (10H), 1.51 (4H). The peak at 1.51 ppm in the $^1$H NMR spectrum corresponds to four protons from two $CH_2$ groups of the adipic acid. Comparison of the integration of this peak with that at 4.87, which corresponds to one CH proton on the oxazolidinone ring of metaxalone, indicates that the cocrystal has a metaxalone:coformer stoichiometry of 1:1.

Example 2

1:0.5 Metaxalone Fumaric Acid Cocrystal 2.1 Preparation of 1:0.5 Metaxalone Fumaric Acid Cocrystal Metaxalone (500 mg) and fumaric acid (262 mg) were weighed into a glass vial. Isopropyl acetate (IPAc, 1.67 ml) was added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour. An additional 100 µl of IPAc was added to filter and the product left to dry under ambient conditions overnight.

2.2 XRPD Characterization of 1:0.5 Metaxalone Fumaric Acid Cocrystal

Figure 5:
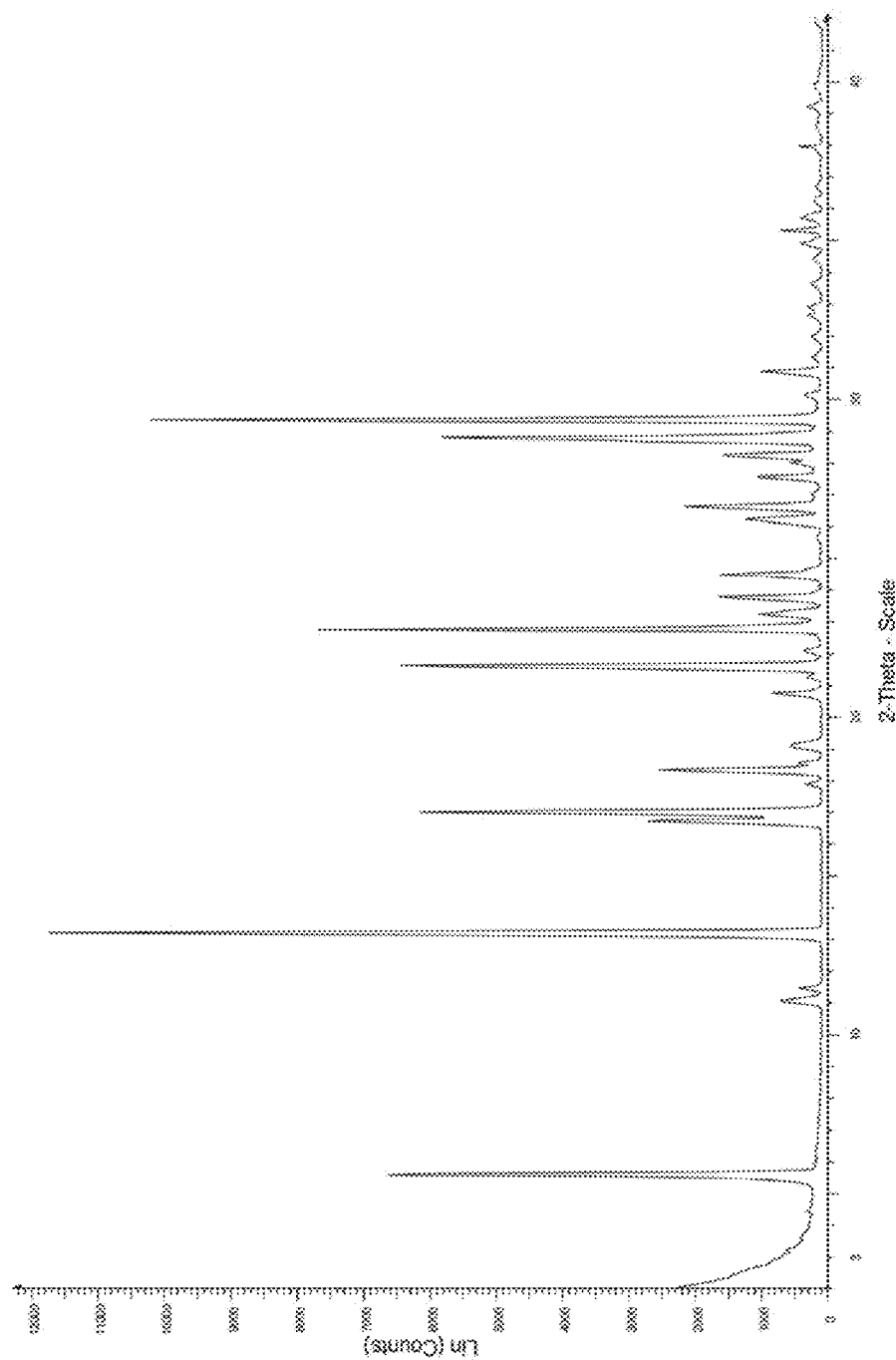
FIG. 5 shows an XRPD pattern for the 1:0.5 metaxalone fumaric acid cocrystal.

The experimental XRPD pattern of the 1:0.5 metaxalone fumaric acid cocrystal is shown in FIG. 5. Table 2 lists the angles, °2θ±0.2°2θ, d-spacing, and intensity of the peaks identified in the XRPD pattern of FIG. 5. The entire list of peaks, or a subset thereof, may be sufficient to characterize the cocrystal. One subset of peaks from FIG. 1 that, individually or in combination, may be used to characterize the 1:0.5 metaxalone fumaric acid cocrystal includes 5.6, 11.0, 13.1, 18.3, 21.6, and 22.7 °2θ±0.2°2θ. The 1:0.5 metaxalone fumaric acid cocrystal may be characterized by a subset of at least three of these peaks.

TABLE 2

| Angle °2θ ± 0.2° 2θ | d value Angstrom | Intensity % |
|---|---|---|
| 5.6 | 15.88 | 56.50 |
| 11.0 | 8.02 | 5.90 |
| 13.1 | 6.73 | 100.00 |
| 16.7 | 5.30 | 23.80 |
| 17.0 | 5.22 | 52.30 |
| 18.3 | 4.84 | 21.50 |
| 19.1 | 4.64 | 4.60 |
| 20.7 | 4.29 | 6.90 |
| 21.6 | 4.11 | 54.80 |
| 22.7 | 3.91 | 65.50 |
| 23.3 | 3.82 | 8.60 |
| 23.8 | 3.74 | 13.90 |
| 24.5 | 3.63 | 13.70 |
| 26.2 | 3.40 | 10.40 |
| 26.6 | 3.35 | 18.30 |
| 27.6 | 3.23 | 8.80 |
| 28.3 | 3.16 | 13.40 |
| 28.8 | 3.01 | 49.40 |
| 29.4 | 3.03 | 87.00 |
| 30.9 | 2.90 | 8.40 |

2.3 SCXRD Characterization of a 1:0.5 Metaxalone Fumaric Acid Cocrystal

The crystal used for single crystal structure determination was prepared as follows:

Approximately 5 mg (estimated by eye) of the metaxalone fumaric acid cocrystal batch prepared as previously described was placed in a 1.5 ml glass HPLC vial and 500 µl of IPA was added. The sample was placed on a shaker at 50° C. for ca. 30 minutes before being removed and 250 µl quickly filtered into a clean 1.5 ml HPLC vial. The vial was covered with film which was then pierced to allow slow evaporation and crystal formation. A suitable single crystal was isolated from the crystals which formed by this method.

Figure 6:
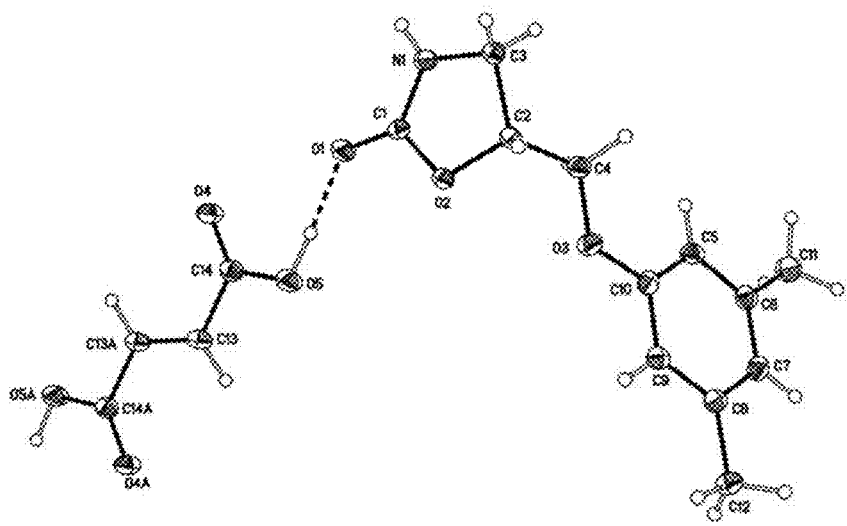
FIG. 6 shows an ORTEP drawing of the 1:0.5 metaxalone fumaric acid cocrystal.
Figure 7:
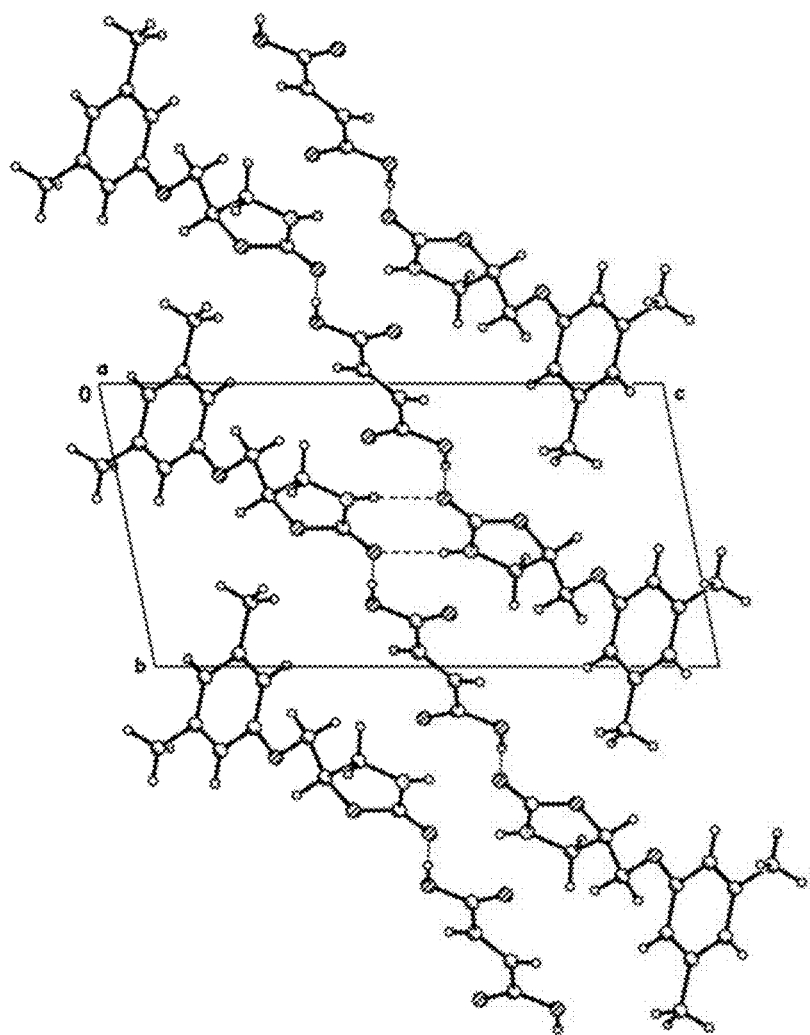
FIG. 7 shows a packing diagram of the 1:0.5 metaxalone fumaric acid cocrystal.
Figure 8:
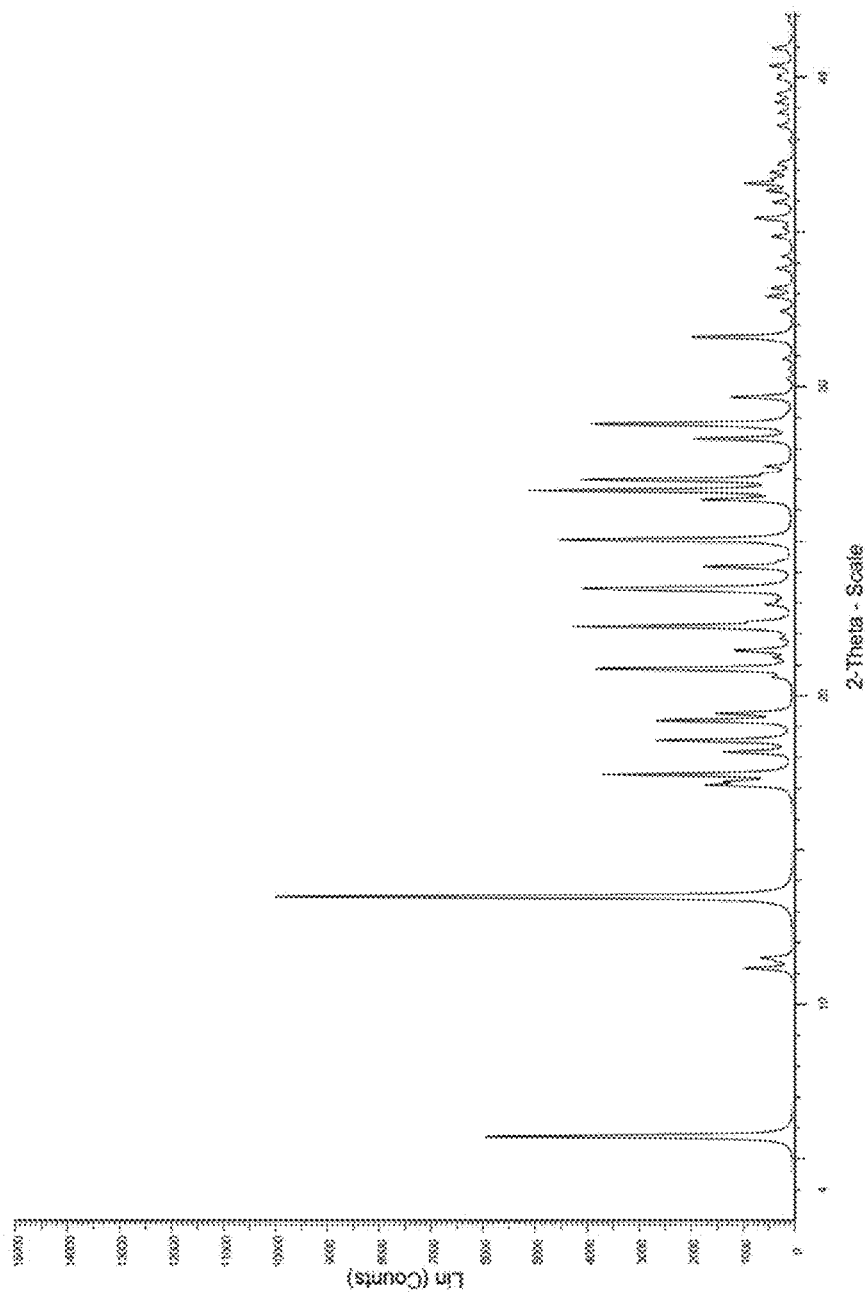
FIG. 8 shows a calculated XRPD pattern for the 1:0.5 metaxalone fumaric acid cocrystal.

The single crystal data and structure refinement parameters are reported in Table 3. FIG. 6 shows an ORTEP drawing of the asymmetric unit from the crystal structure of the 1:0.5 metaxalone fumaric acid cocrystal showing the atom numbering scheme employed. Anisotropic atomic displacement ellipsoids for the non-hydrogen atoms are shown at the 50% probability level and hydrogen atoms are displayed as spheres of arbitrary radius. Atoms of the fumaric acid coformer labeled with the suffix A, which are bound to a second metaxalone molecule, were generated through a symmetry operation. FIG. 7 shows the crystal packing of the 1:0.5 metaxalone fumaric acid cocrystal; the view is down the a-axis of the unit cell. The calculated XRPD pattern based on the single crystal data and structure for the 1:0.5 metaxalone fumaric acid cocrystal is shown in FIG. 8. It is also noted that there are some small temperature shifts in some of the peaks owing to the fact that the experimental XRPD pattern was collected at room temperature and the calculated XRPD pattern is derived from data collected at 120K. There are also small intensity differences owing to preferred orientation effects, present in the experimental pattern.

TABLE 3

| | |
|---|---|
| Molecular formula | $C_{14}H_{17}NO_5$ |
| Molecular weight | 279.29 |
| Crystal System | Triclinic |
| Space Group | P-1 |
| Unit Cell Dimensions | a = 5.3377(3) Å |
| | b = 8.1311(5) Å |
| | c = 15.9315(8) Å |
| | α = 78.303(5)° |
| | β = 84.012(4)° |
| | γ = 84.419(4)° |
| Cell Volume | 671.34(7) Å$^3$ |
| Z | 2 |
| Temperature | 120(1) K |
| Radiation Wavelength/type | 1.54178 Å/CuK\α |
| Goodness of fit | 1.001 |
| R factor | 0.0335 |
| Morphology | Colourless block |

2.4 DSC of 1:0.5 Metaxalone Fumaric Acid Cocrystal

Figure 9:
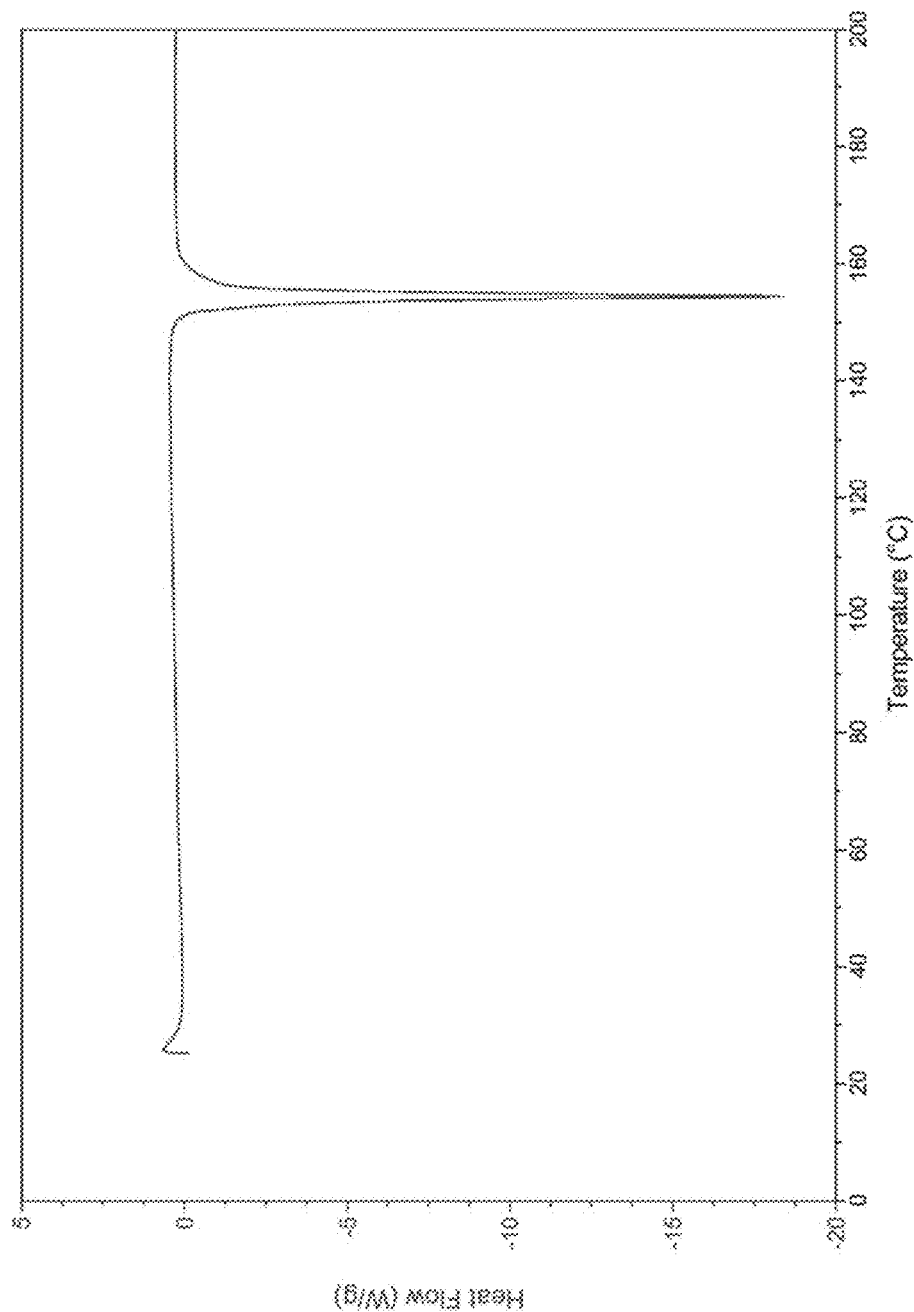
FIG. 9 shows a DSC trace for the 1:0.5 metaxalone fumaric acid cocrystal.

The differential scanning calorimetry (DSC) trace, FIG. 9, shows a single endotherm with an onset temperature of 153.45° C. and a peak maximum of 154.34° C.

2.5 TGA of 1:0.5 Metaxalone Fumaric Acid Cocrystal

Figure 10:
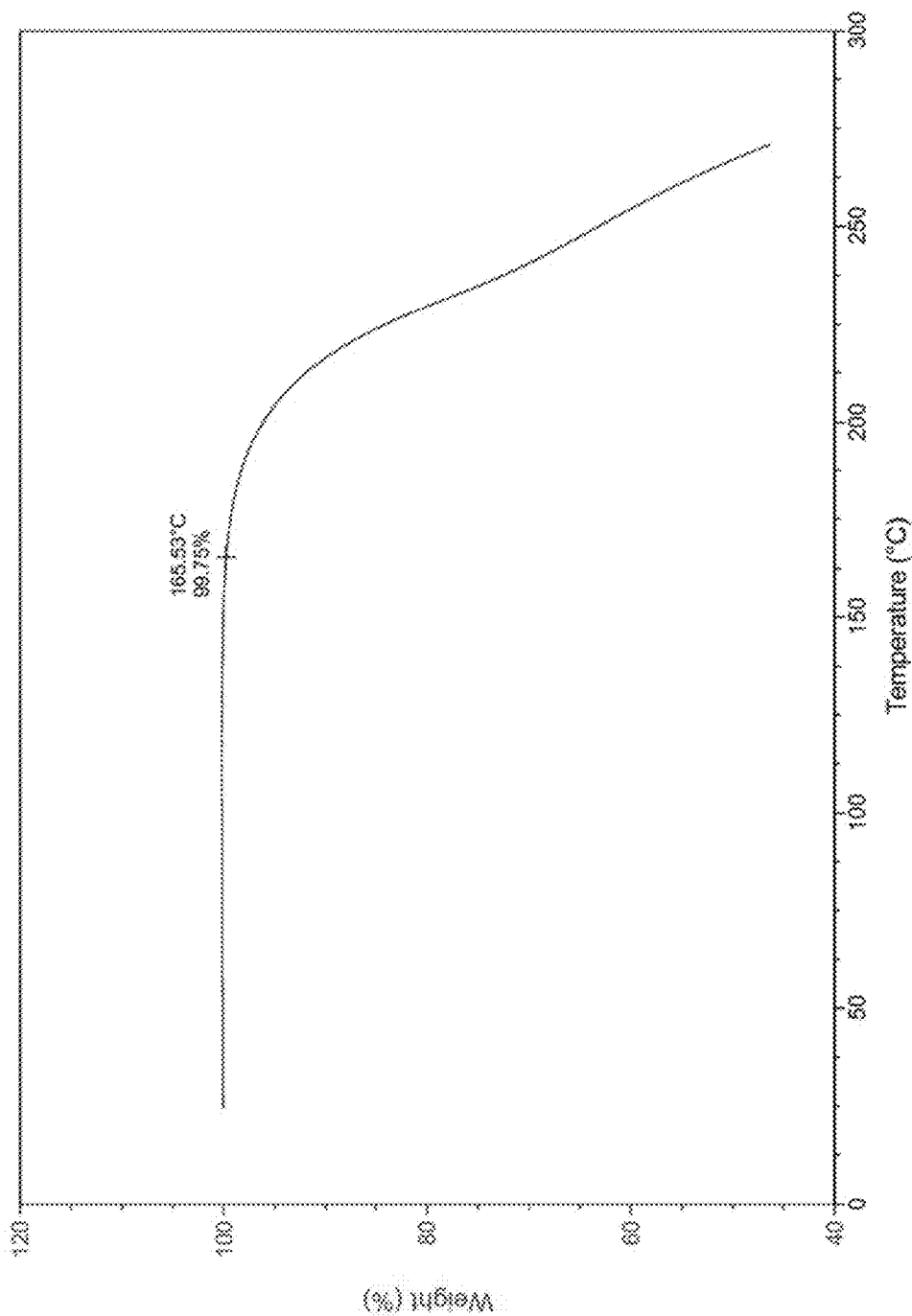
FIG. 10 shows a TGA trace for the 1:0.5 metaxalone fumaric acid cocrystal.

The thermal gravimetric analysis (TGA) trace, FIG. 10, shows no significant weight loss prior to degradation with 99.75% weight remaining at 165.53° C.

2.6 NMR Spectrum of 1:0.5 Metaxalone Fumaric Acid Cocrystal

Figure 11:
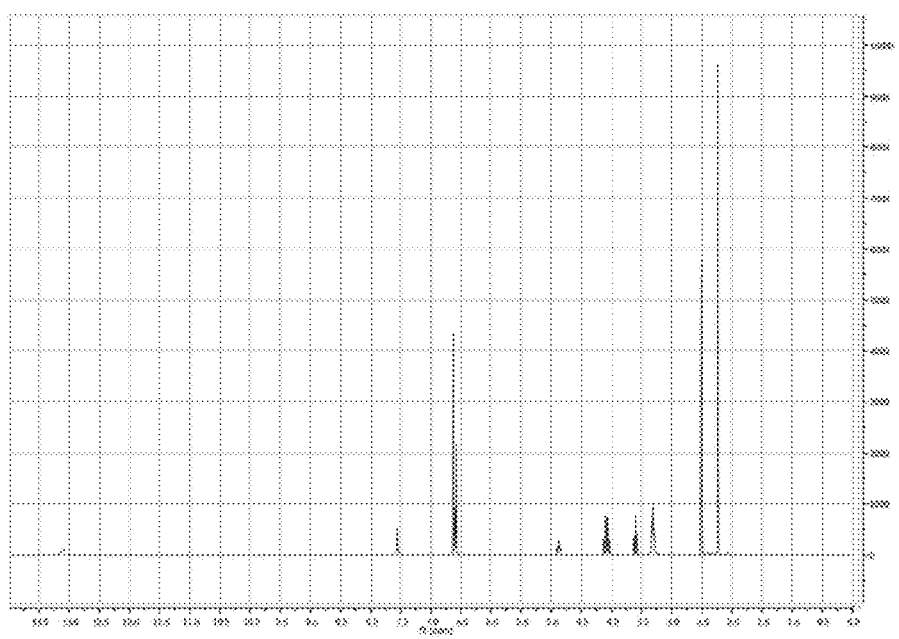
FIG. 11 shows the $^1$H NMR spectrum of 1:0.5 metaxalone fumaric acid cocrystal.

The $^1$H NMR spectrum of the metaxalone fumaric acid cocrystal, shown in FIG. 11, displays the following peaks: $^1$H NMR (400 MHz, d6-DMSO) δ: 13.12 (1H), 7.56 (1H), 6.63 (1H), 6.59 (3H), 4.86 (1H), 4.08 (2H), 3.60 (1H), 3.31 (1H), 2.23 (6H). The peak at 6.63 ppm in the $^1$H NMR spectrum corresponds to the two protons on the double bond of fumaric acid. Comparison of the integration of this peak with that at 4.86, which corresponds to one CH proton on the oxazolidinone ring of metaxalone, indicates that the cocrystal has a metaxalone:coformer stoichiometry of 1:0.5.

2.7 Gram Scale Preparation of 1:0.5 Metaxalone Fumaric Acid Cocrystals

Metaxalone (3.00 g) and fumaric acid (787 mg) were weighed into a round bottom flask. IPAc (10 ml) was added to the flask. With stirring the resultant slurry was heated to ~60° C. for 30 minutes before being stirred at room temperature for 3 days. The product was filtered under vacuum and air dried overnight. XRPD analysis confirmed the product to be the 1:0.5 metaxalone fumaric acid cocrystal.

Example 3

Metaxalone 1:1 Salicylic Acid Cocrystal 3.1 Preparation of 1:1 Metaxalone Salicylic Acid Cocrystal Metaxalone (100 mg) and salicylic acid (62.4 mg) were placed in a stainless steel ball mill. Water (2 drops) was added. The two components were ground together for 60 minutes at 20 Hz. The product was removed from the mill and left to dry under ambient temperatures overnight.

3.2 XRPD Characterization of 1:1 Metaxalone Salicylic Acid Cocrystal

Figure 12:
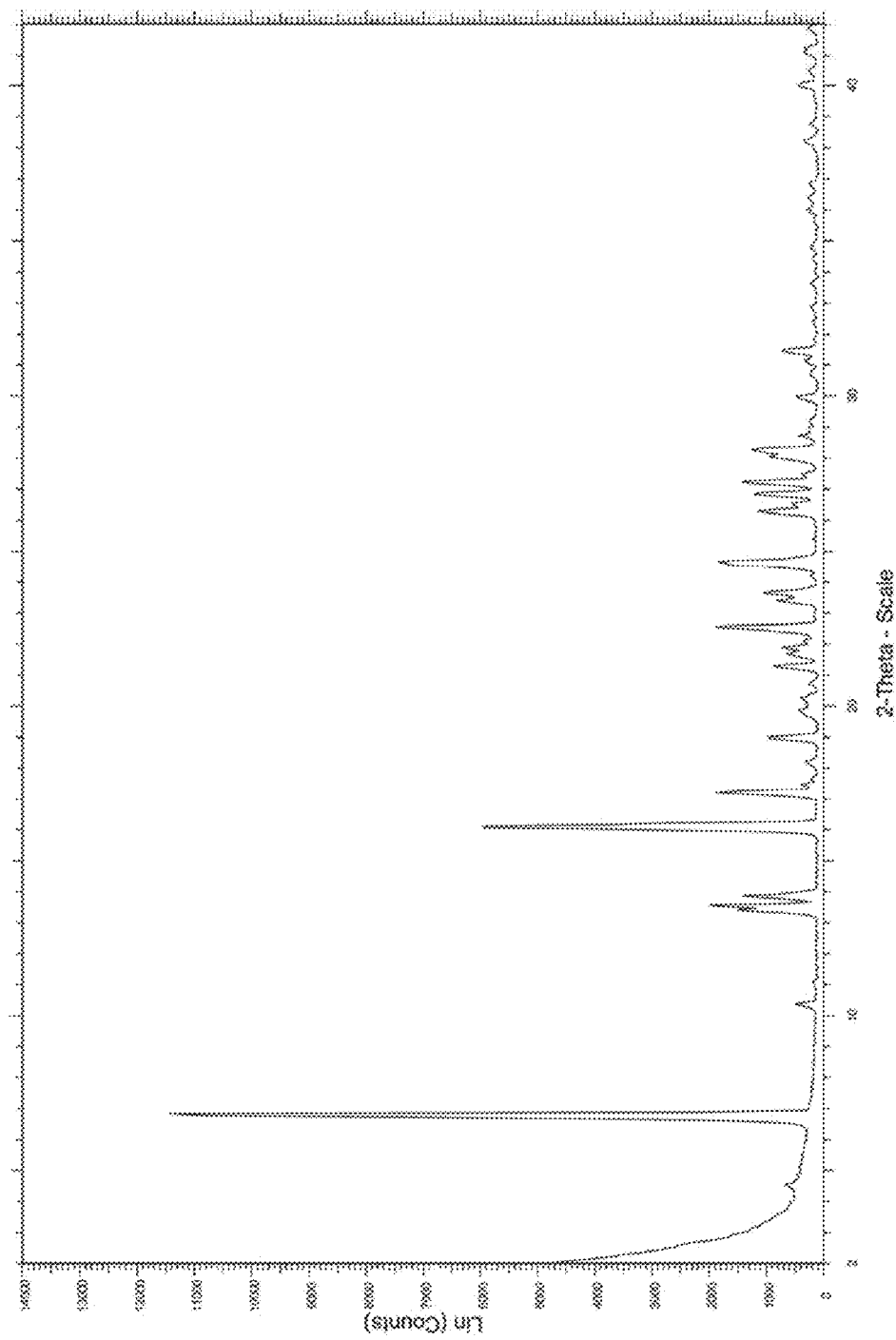
FIG. 12 shows an XRPD pattern for the 1:1 metaxalone salicylic acid cocrystal.

The experimental XRPD pattern of the 1:1 metaxalone salicylic acid cocrystal is shown in FIG. 12. Table 4 lists the angles, °2θ±0.2°2θ, d-spacing, and intensity of the peaks identified in the XRPD pattern of FIG. 12. The entire list of peaks, or a subset thereof, may be sufficient to characterize the cocrystal. One subset of peaks from FIG. 12 that, individually or in combination, may be used to characterize the 1:1 metaxalone salicylic acid cocrystal includes 6.8, 16.1, 17.2, 22.6, and 24.6 °2θ±0.2°2θ. The 1:1 metaxalone salicylic acid cocrystal may be characterized by a subset of at least three of these peaks.

TABLE 4

| Angle °2θ ± 0.2° 2θ | d value Angstom | Intensity % |
| --- | --- | --- |
| 6.8 | 13.02 | 100.00 |
| 10.3 | 8.55 | 4.00 |
| 13.4 | 6.61 | 13.00 |
| 13.5 | 6.56 | 17.20 |
| 13.8 | 6.41 | 12.10 |
| 16.1 | 5.51 | 51.90 |
| 17.2 | 5.15 | 16.20 |
| 19.0 | 4.67 | 8.20 |
| 21.3 | 4.17 | 7.40 |
| 21.7 | 4.09 | 5.40 |
| 21.9 | 4.06 | 6.10 |
| 22.6 | 3.94 | 16.20 |
| 23.4 | 3.80 | 6.80 |
| 23.7 | 3.76 | 9.20 |
| 24.6 | 3.61 | 15.90 |
| 26.3 | 3.39 | 9.80 |
| 26.5 | 3.36 | 4.50 |
| 26.9 | 3.32 | 10.40 |
| 27.2 | 3.27 | 12.20 |
| 28.1 | 3.18 | 7.90 |
| 28.3 | 3.15 | 10.70 |
| 31.5 | 2.84 | 6.10 |

Figure 15:
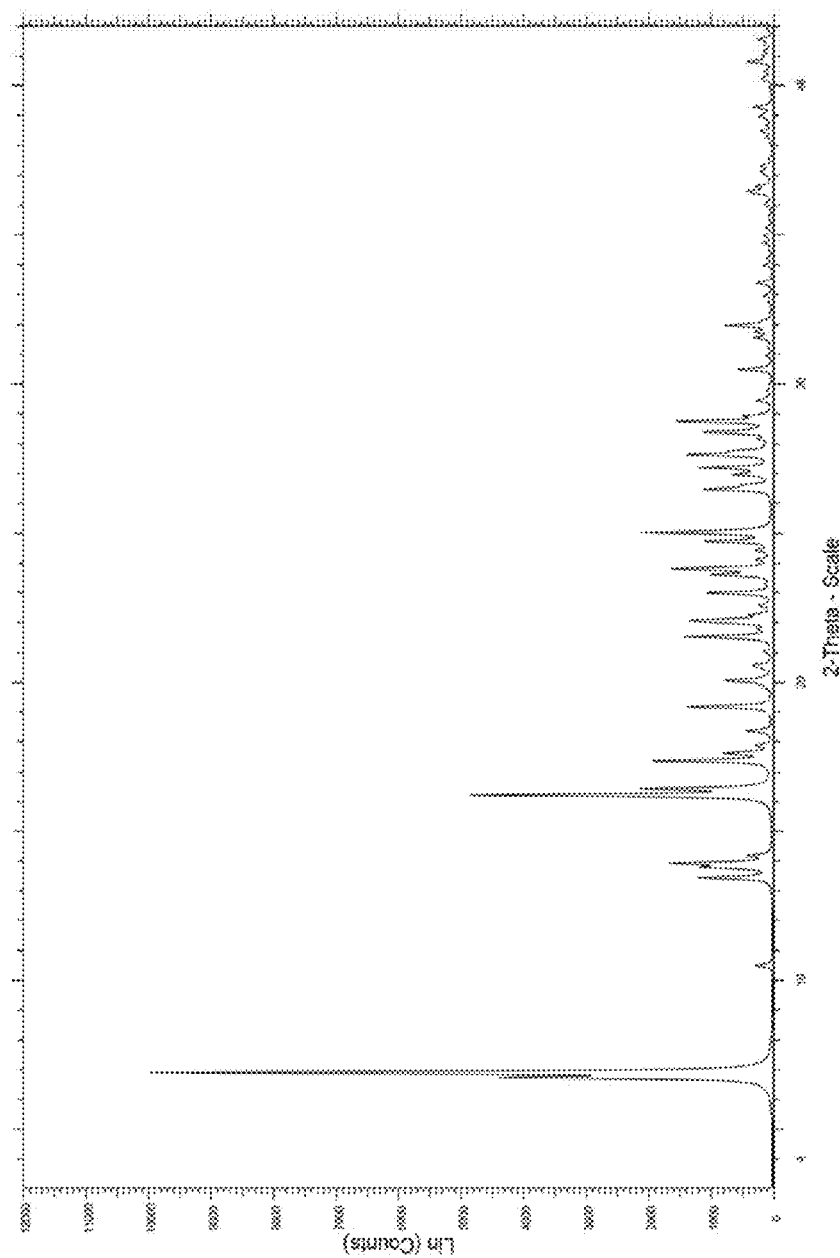
FIG. 15 shows a calculated XRPD pattern for the 1:1 metaxalone salicylic acid cocrystal.

Analysis of the experimental XRPD pattern in FIG. 12, and comparison with the calculated XRPD pattern, FIG. 15, indicated that there may be very small traces of the metaxalone free base present in the sample, although this is not evident from the DSC trace or $^1$H NMR spectrum (below).

3.3 SCXRD Characterization of 1:1 Metaxalone Salicylic Acid Cocrystal

The crystal used for single crystal structure determination was prepared as follows:

1.1 equivalents of salicylic acid were added to 75 mg of metaxalone in a 1.5 ml glass HPLC vial. Enough solvent (water) was then added to cover the solid (5500. The sample was then subjected to sonication using a 100 W ultrasonic probe for 20 minutes using a pulse series of 10 s on and 4 s off. Prior to filtration an additional aliquot of cold solvent (water, 100 µl) was added to the vial. The sample was then filtered under vacuum for ca. 2 hours. After this time the sample was removed from the vacuum and dried at room temperature for at least 16 hours. A crystal was then isolated from the bulk dried material and a single crystal structure on this crystal determined proving it to be a 1:1 metaxalone salicylic acid cocrystal.

Figure 13:
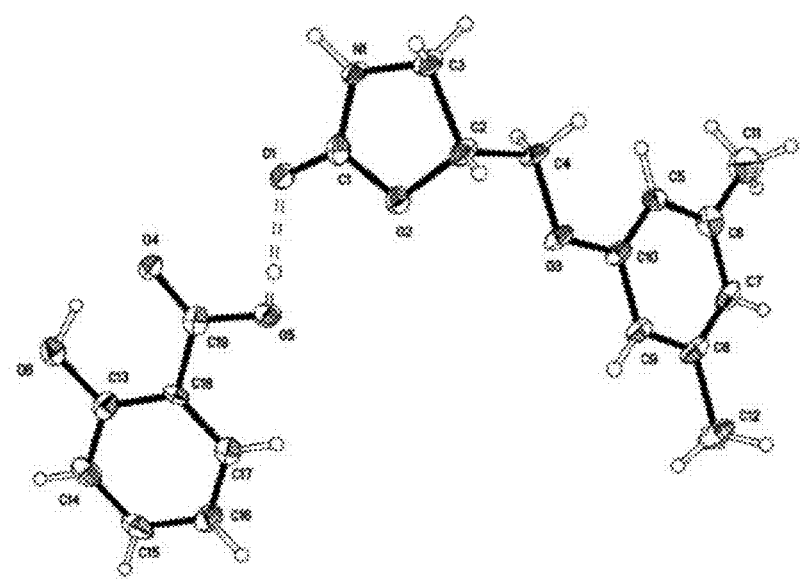
FIG. 13 shows an ORTEP drawing of the 1:1 metaxalone salicylic acid cocrystal.
Figure 14:
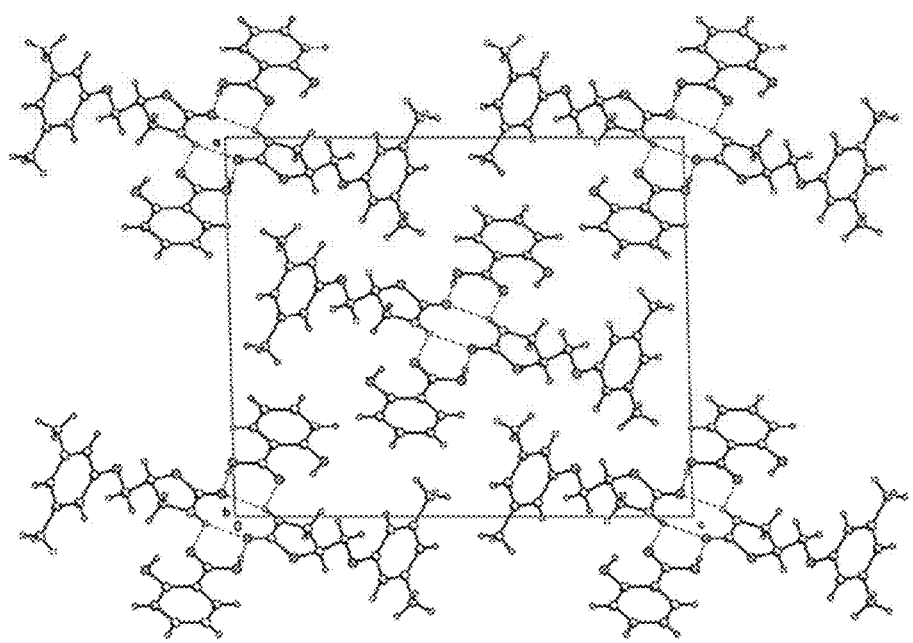
FIG. 14 shows a packing diagram of the 1:1 metaxalone salicylic acid cocrystal.

The single crystal data and structure refinement parameters are reported in Table 5. FIG. 13 is an ORTEP drawing of the asymmetric unit from the crystal structure of the 1:1 metaxalone salicylic acid cocrystal showing the atom numbering scheme employed. Anisotropic atomic displacement ellipsoids for the non-hydrogen atoms are shown at the 50% probability level and hydrogen atoms are displayed as spheres of arbitrary radius. FIG. 14 shows the crystal packing of the 1:1 metaxalone salicylic acid cocrystal; the view is down the b-axis of the unit cell. The calculated XRPD pattern based on the single crystal data and structure for the 1:1 metaxalone salicylic acid cocrystal is shown in FIG. 15. Comparison of the simulated powder pattern of this crystal with the experimental powder pattern of the bulk material showed that the material was non-homogeneous and consisted of the cocrystal and trace amounts of metaxalone. It is also noted that there are some small temperature shifts in some of the peaks owing to the fact that the experimental XRPD pattern was collected at room temperature and the calculated XRPD pattern is derived from data collected at 120K. There are also small intensity differences owing to preferred orientation effects, present in the experimental pattern.

TABLE 5

| | |
| --- | --- |
| Molecular Formula | $C_{19}H_{21}NO_6$ |
| Molecular weight | 359.37 |
| Crystal System | Monoclinic |
| Space Group | P21/n |
| Unit Cell Dimensions | a = 16.8887(14) Å |
| | b = 5.1902(5) Å |
| | c = 20.410(2) Å |
| | α = 90.00° |
| | β = 91.491(9)° |
| | γ = 90.00° |
| Cell Volume | 1788.4(3) Å$^3$ |
| Z | 4 |
| Temperature | 120(1) K |
| Radiation Wavelength/type | 1.54178 Å/CuK\α |
| Goodness of fit | 1.000 |
| R factor | 0.0534 |
| Morphology | Colourless lath |

3.4 DSC of 1:1 Metaxalone Salicylic Acid Cocrystal

Figure 16:
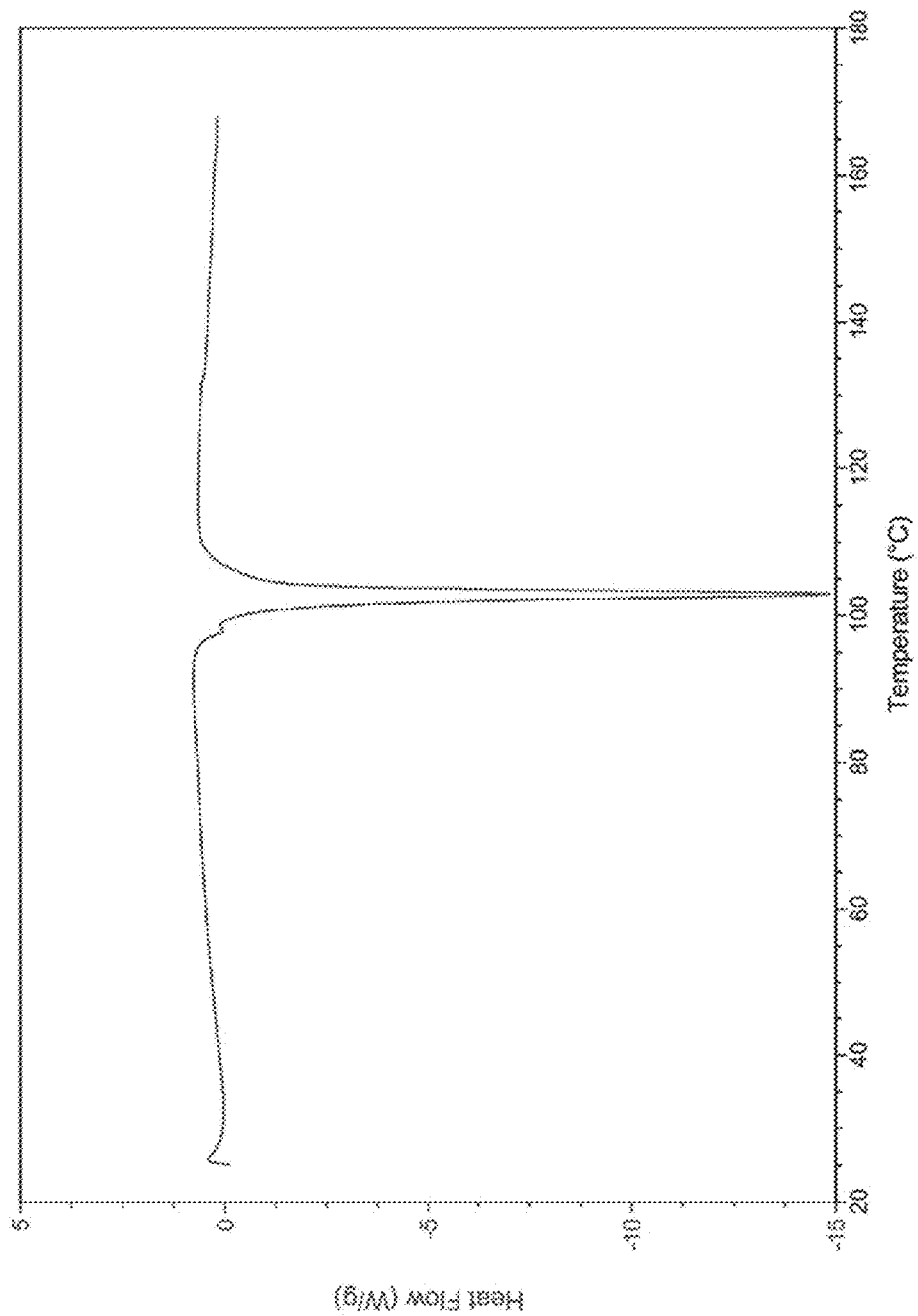
FIG. 16 shows a DSC trace for the 1:1 metaxalone salicylic acid cocrystal.

The differential scanning calorimetry (DSC) trace, FIG. 16, shows a melting endotherm with an onset temperature of 101.55° C. and a peak maximum of 102.89° C.

3.5 TGA of 1:1 Metaxalone Salicylic Acid Cocrystal

Figure 17:
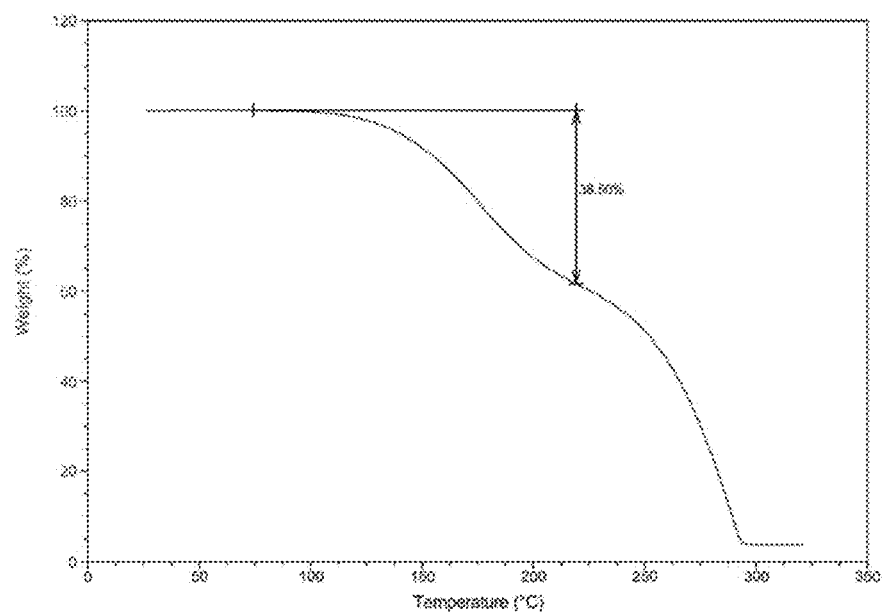
FIG. 17 shows a TGA trace for the 1:1 metaxalone salicylic acid cocrystal.

In the thermal gravimetric analysis (TGA), FIG. 17, it can be seen that after the cocrystal melt temperature there is a 38.5% weight loss followed by apparent sublimation.

3.6 $^1$H NMR Spectrum of 1:1 Metaxalone Salicylic Acid Cocrystal

Figure 18:
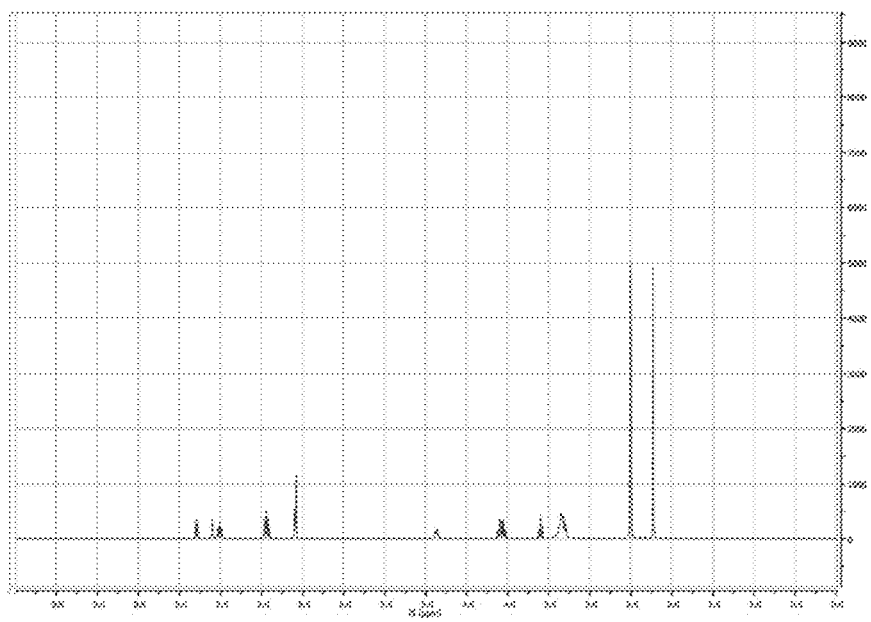
FIG. 18 shows the $^1$H NMR spectrum of 1:1 metaxalone salicylic acid cocrystal.

The $^1$H NMR spectrum of the metaxalone fumaric acid cocrystal, shown in FIG. 18, displays the following peaks: $^1$H NMR (400 MHz, d6-DMSO) δ: 7.80 (1H), 7.60 (1H), 7.51 (1H), 6.93 (2H), 6.59 (3H) 4.88 (1H), 4.08 (2H), 3.60 (1H), 3.31 (1H), 2.23 (6H). The peak at 7.80 ppm in the $^1$H NMR spectrum corresponds to one aromatic proton on the salicylic acid. Comparison of the integration of this peak with that at 4.88, which corresponds to one CH proton on the oxazolidinone ring of metaxalone, indicates that the cocrystal has a metaxalone:coformer stoichiometry of 1:1.

Example 4

1:0.5 Metaxalone Succinic Acid Cocrystal 4.1 Preparation of 1:0.5 Metaxalone Succinic Acid Cocrystal Metaxalone (500 mg) was weighed into a glass vial. 1.67 ml of a hot saturated solution of succinic acid in THF was then added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour. An additional 200 µl of THF was added to filter and the product left to dry under ambient conditions overnight.

4.2 XRPD Characterization of 1:0.5 Metaxalone Succinic Acid Cocrystal

Figure 19:
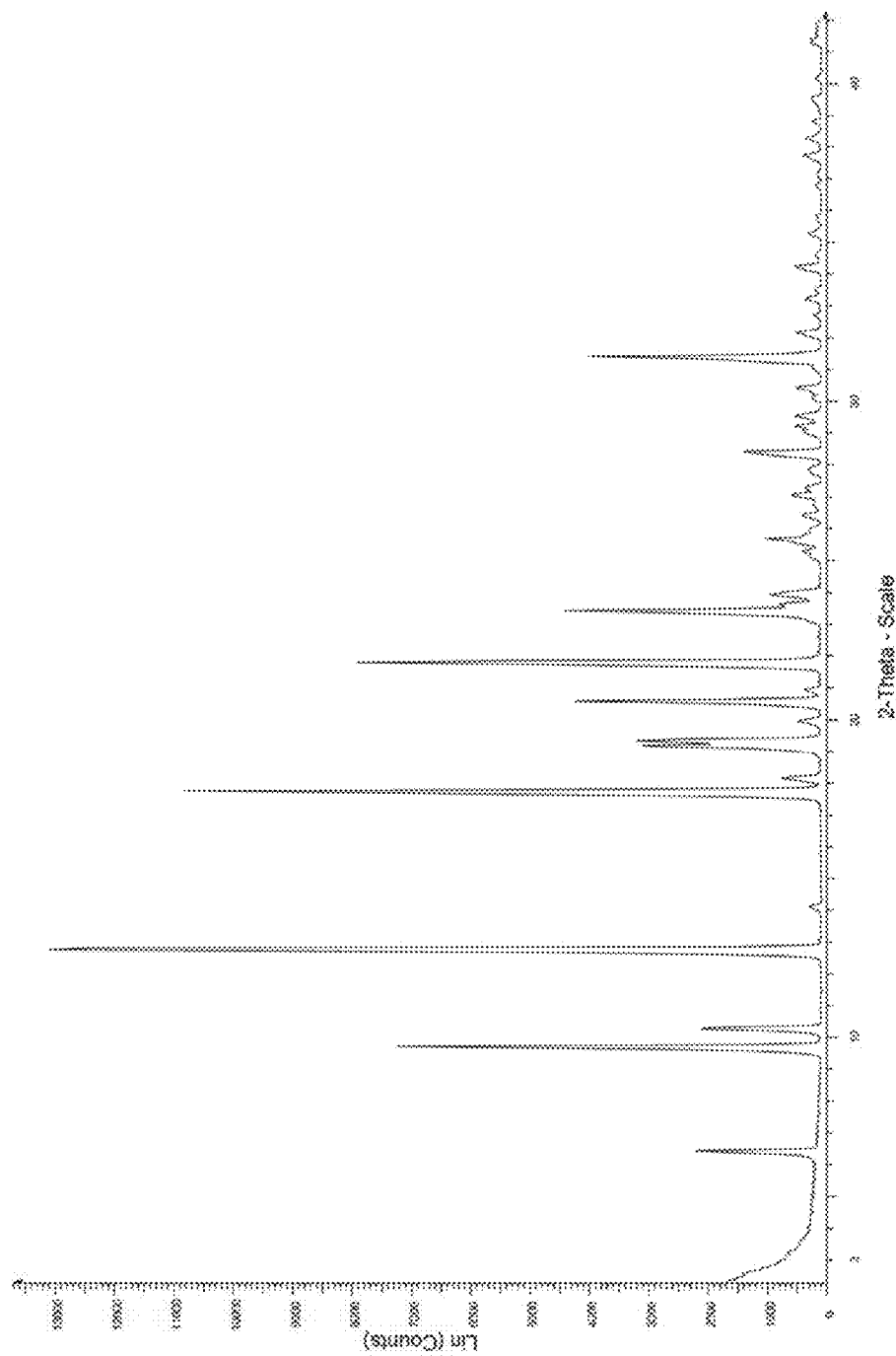
FIG. 19 shows an XRPD pattern for the 1:0.5 metaxalone succinic acid cocrystal.

The experimental XRPD pattern of the 1:0.5 metaxalone succinic acid cocrystal is shown in FIG. 19. Table 6 lists the angles, °2θ±0.2°2θ, d-spacing, and intensity of the peaks identified in the XRPD pattern of FIG. 19. The entire list of peaks, or a subset thereof, may be sufficient to characterize the cocrystal. One subset of peaks from FIG. 19 that, individually or in combination, may be used to characterize the 1:0.5 metaxalone succinic acid cocrystal includes 6.4, 9.7, 10.2, 12.7, 20.6, and 21.7 °2θ±0.2°2θ. The 1:0.5 metaxalone succinic acid cocrystal may be characterized by a subset of at least three of these peaks.

TABLE 6

| Angle °2θ ± 0.2° 2θ | d value Angstrom | Intensity % |
|---|---|---|
| 6.4 | 13.82 | 16.70 |
| 9.7 | 9.14 | 55.40 |
| 10.2 | 8.63 | 16.00 |
| 12.7 | 6.95 | 100.00 |
| 17.7 | 5.00 | 82.60 |
| 18.1 | 4.89 | 5.60 |
| 19.2 | 4.62 | 24.10 |
| 19.4 | 4.58 | 24.70 |
| 20.6 | 4.31 | 32.20 |
| 21.7 | 4.09 | 60.40 |
| 23.5 | 3.79 | 33.70 |
| 23.9 | 3.71 | 7.10 |
| 25.7 | 3.47 | 7.60 |
| 27.1 | 3.29 | 4.40 |
| 28.4 | 3.14 | 10.50 |
| 31.4 | 2.85 | 30.40 |

4.3 SCXRD Characterization of 1:0.5 Metaxalone Succinic Acid Cocrystal

The crystal used for single crystal structure determination was prepared as follows:

250 µl of a hot saturated solution of succinic acid in THF was pipetted into a 1.5 ml glass HPLC vial. Metaxalone was then gradually added until a slurry was obtained. The sample was left to mature for five days on a four hourly heat/cool (50° C./RT) cycle. In order to filter the bulk sample, an additional aliquot of cold solvent (THF, 100 µl) was added to the vial. The sample was then filtered under vacuum for ca. 2 hours. After this time the sample was removed from the vacuum and stored at room temperature to dry for at least 16 hours.

A suitable single crystal was isolated from the bulk dried material and determined by SCXRD analysis to be a 1:0.5 metaxalone succinic acid cocrystal. The single crystal data and structure refinement parameters are reported in Table 7.

Figure 20:
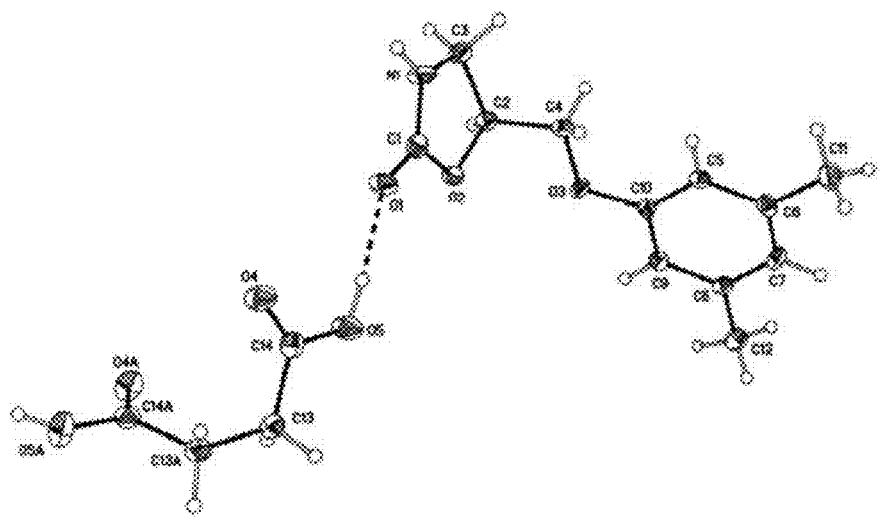
FIG. 20 shows an ORTEP drawing of the 1:0.5 metaxalone succinic acid cocrystal.
Figure 21:
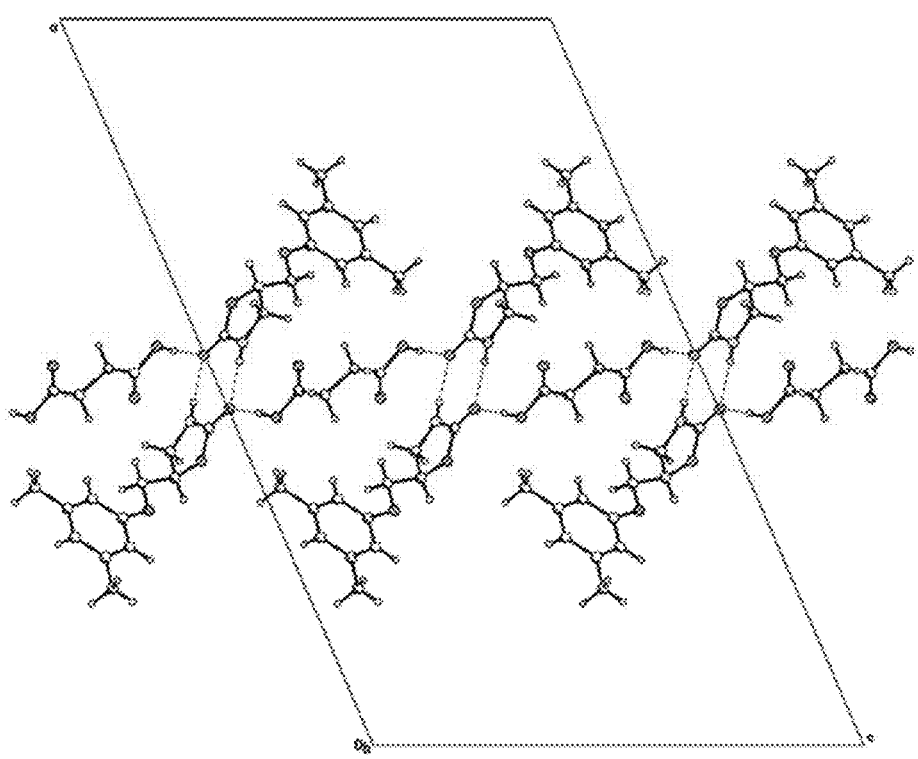
FIG. 21 shows a packing diagram of the 1:0.5 metaxalone succinic acid cocrystal.
Figure 22:
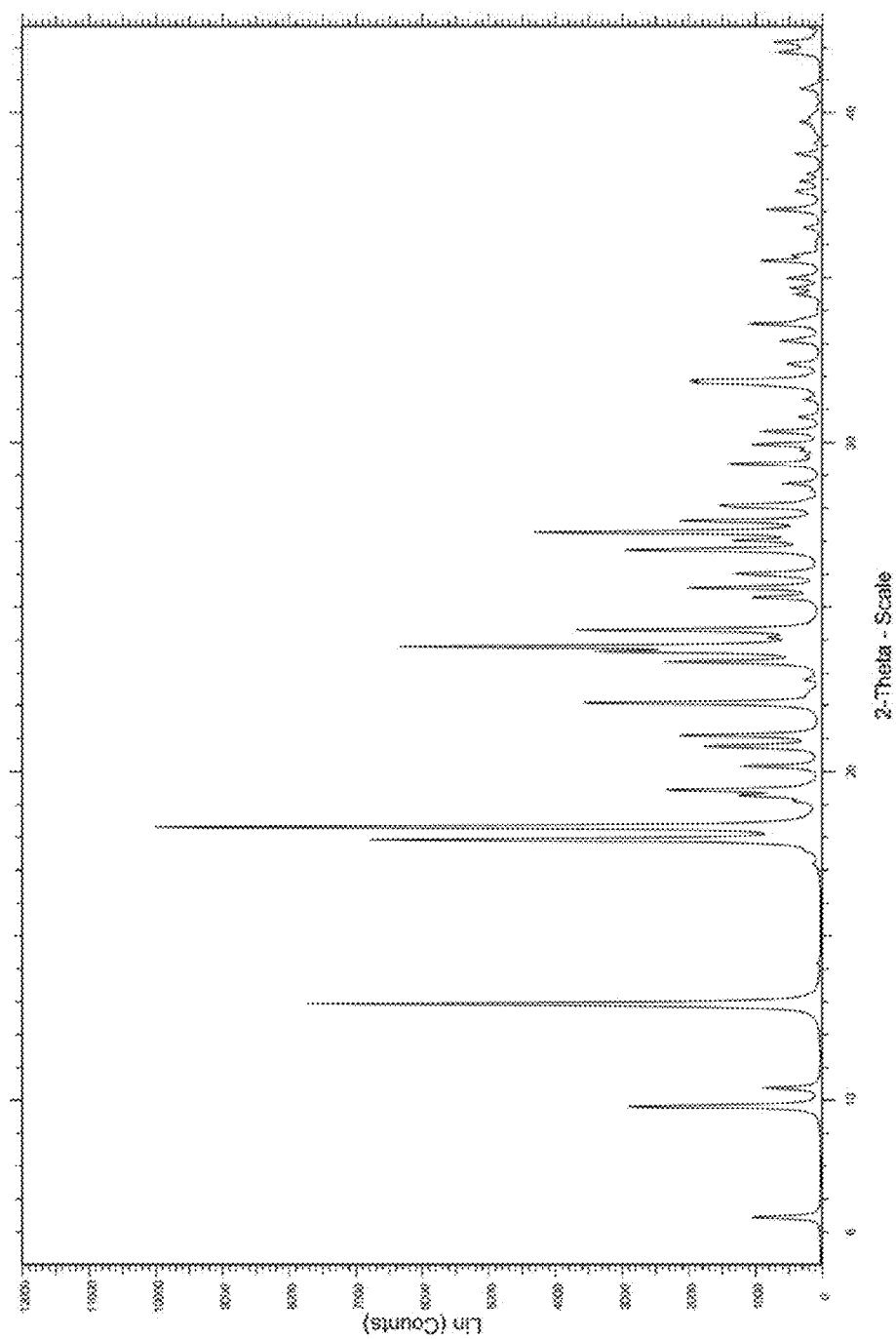
FIG. 22 shows a calculated XRPD pattern for the 1:0.5 metaxalone succinic acid cocrystal.

FIG. 20 shows an ORTEP drawing of the asymmetric unit from the crystal structure of the metaxalone succinic acid cocrystal showing the atom numbering scheme employed. Anisotropic atomic displacement ellipsoids for the non-hydrogen atoms are shown at the 50% probability level and hydrogen atoms are displayed as spheres of arbitrary radius. Atoms of the coformer labeled with the suffix A, which are bound to a second metaxalone molecule, were generated through a symmetry operation. FIG. 21 shows the crystal packing of 1:0.5 metaxalone succinic acid cocrystal; the view is down the b-axis of the unit cell. The calculated XRPD pattern based on the single crystal data and structure for the 1:0.5 metaxalone succinic acid cocrystal is shown in FIG. 22. It is also noted that there are some small temperature shifts in some of the peaks owing to the fact that the experimental XRPD pattern was collected at room temperature and the calculated XRPD pattern is derived from data collected at 120K. There are also small intensity differences owing to preferred orientation effects, present in the experimental pattern.

TABLE 7

| | |
|---|---|
| Molecular formula | $C_{14}H_{18}NO_5$ |
| Molecular weight | 280.29 |
| Crystal System | Monoclinic |
| Space Group | C2/c |
| Unit Cell Dimensions | a = 30.063(2) Å |
| | b = 5.2567(3) Å |
| | c = 18.6125(16) Å |
| | α = 90.00° |
| | β = 113.286(10)° |
| | γ = 90.00° |
| Cell Volume | 2701.7(3) Å$^3$ |
| Z | 8 |
| Temperature | 120(1) K |
| Radiation Wavelength | 0.7107 Å |
| Goodness of fit | 1.003 |
| R factor | 0.0378 |
| Morphology | Colourless lath |

4.4 DSC of 1:0.5 Metaxalone Succinic Acid Cocrystal

Figure 23:
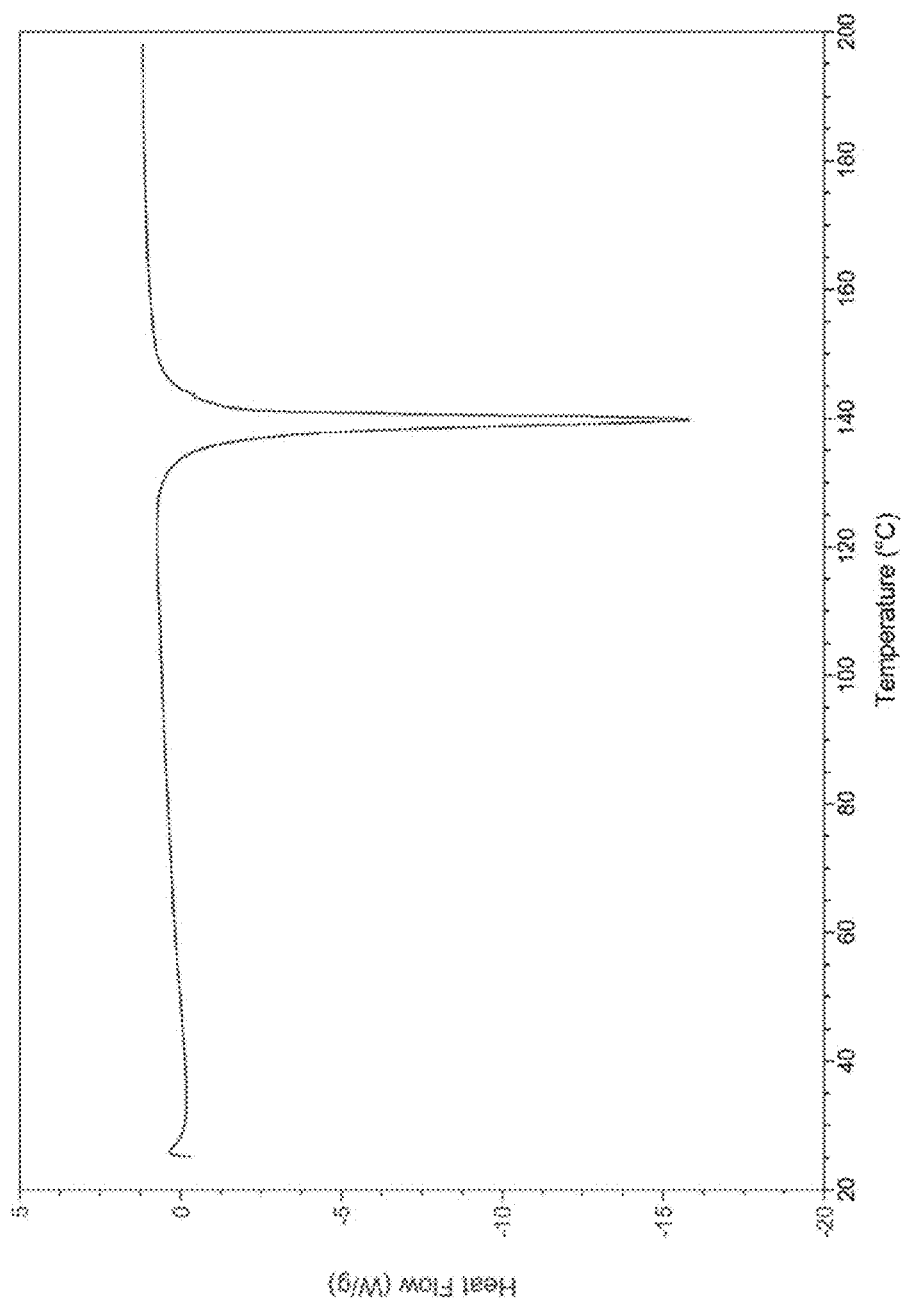
FIG. 23 shows a DSC trace for the 1:0.5 metaxalone succinic acid cocrystal.

The differential scanning calorimetry (DSC) trace, FIG. 23, shows a single endotherm with an onset temperature of 137.44° C. and a peak maximum of 148.54° C.

4.5 TGA of 1:0.5 Metaxalone Succinic Acid Cocrystal

Figure 24:
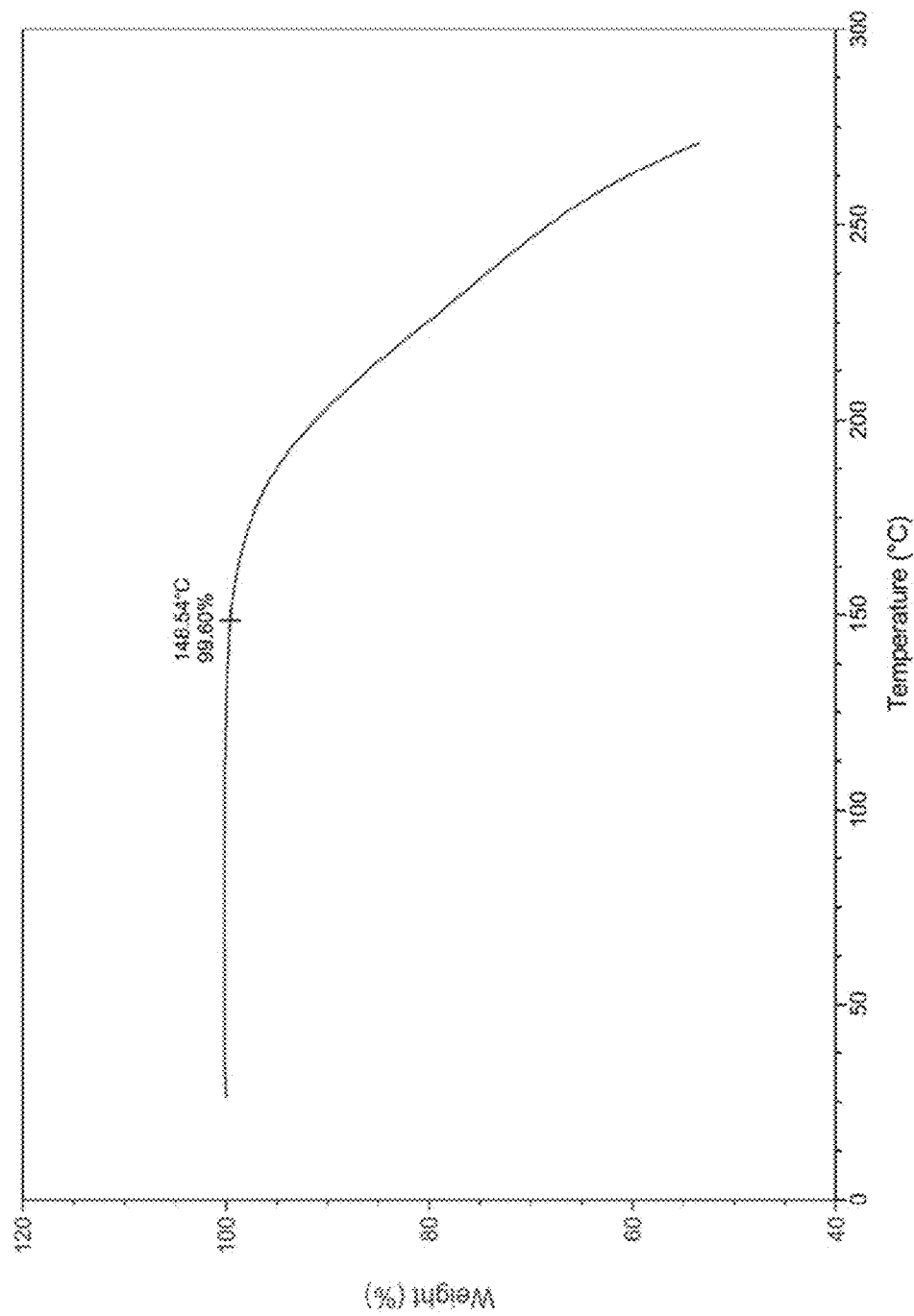
FIG. 24 shows a TGA trace for the 1:0.5 metaxalone succinic acid cocrystal.

The thermal gravimetric analysis (TGA) trace, FIG. 24, shows no significant weight loss prior to degradation with 99.6% weight remaining at 148.54° C.

4.6 $^1$H NMR Spectrum of 1:0.5 Metaxalone Succinic Acid Cocrystal

Figure 25:
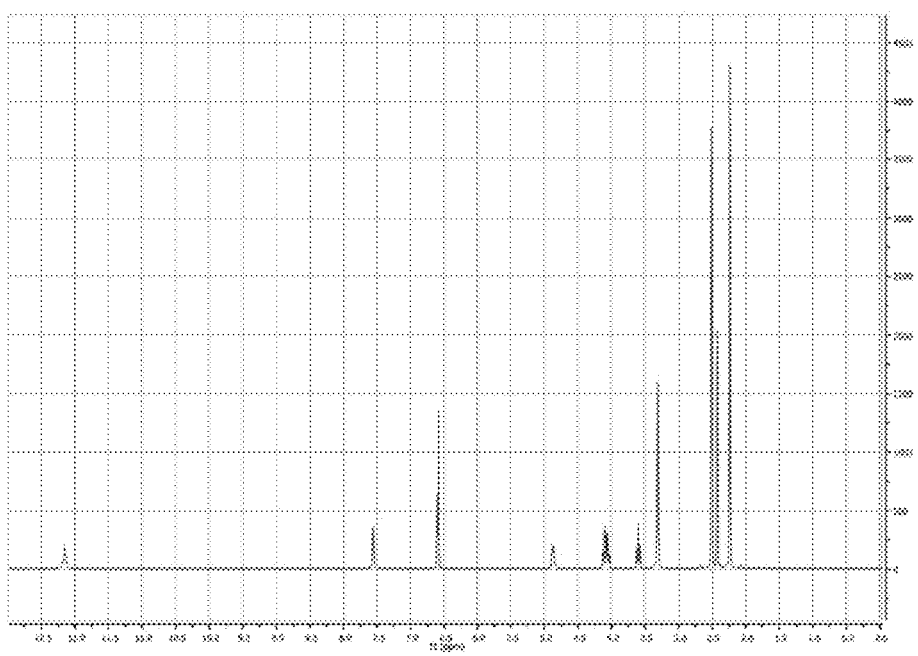
FIG. 25 shows the $^1$H NMR spectrum of 1:0.5 metaxalone succinic acid cocrystal.

The $^1$H NMR spectrum of the metaxalone succinic acid cocrystal, shown in FIG. 25, displays the following peaks: $^1$H NMR (400 MHz, d6-DMSO) δ: 12.15 (1H), 7.56 (1H), 6.59 (3H), 4.87 (1H), 4.10 (2H), 3.60 (1H), 3.31 (1H), 2.42 (2H), 2.23 (6H). The peak at 2.42 ppm in the $^1$H NMR spectrum corresponds to the four protons from the two CH$_2$ groups of succinic acid. Comparison of the integration of this peak with that at 4.87, which corresponds to the one CH proton on the oxazolidinone ring of metaxalone, indicates that the cocrystal has a metaxalone:coformer stoichiometry of 1:0.5.

4.7 Gram Scale Preparation of 1:0.5 Metaxalone Succinic Acid Cocrystal

Metaxalone (3.00 g) was placed in a round bottom flask. 10 ml of a saturated solution of succinic acid in THF was added. With stirring the resultant slurry was gradually heated using a water bath until all solid had dissolved to give a clear colourless solution. The water bath was then removed and the solution gradually cooled back to room temperature resulting in the precipitation of a white solid. The slurry was then allowed to stir at room temperature for 4 days before the product was filtered under vacuum and air dried overnight. XRPD analysis confirmed the product to be the 1:0.5 metaxalone succinic acid cocrystal.

Example 5

1:0.5 Metaxalone Maleic Acid Cocrystal 5.1 Preparation of 1:0.5 Metaxalone Maleic Acid Cocrystal Metaxalone (500 mg) was weighed into a glass vial. 2 ml of a saturated solution of maleic acid in EtOAc was then added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour. An additional 200 μl of EtOAc was added to filter and the product left to dry under ambient conditions overnight.

5.2 XRPD Characterization of 1:0.5 Metaxalone Maleic Acid Cocrystal

Figure 26:
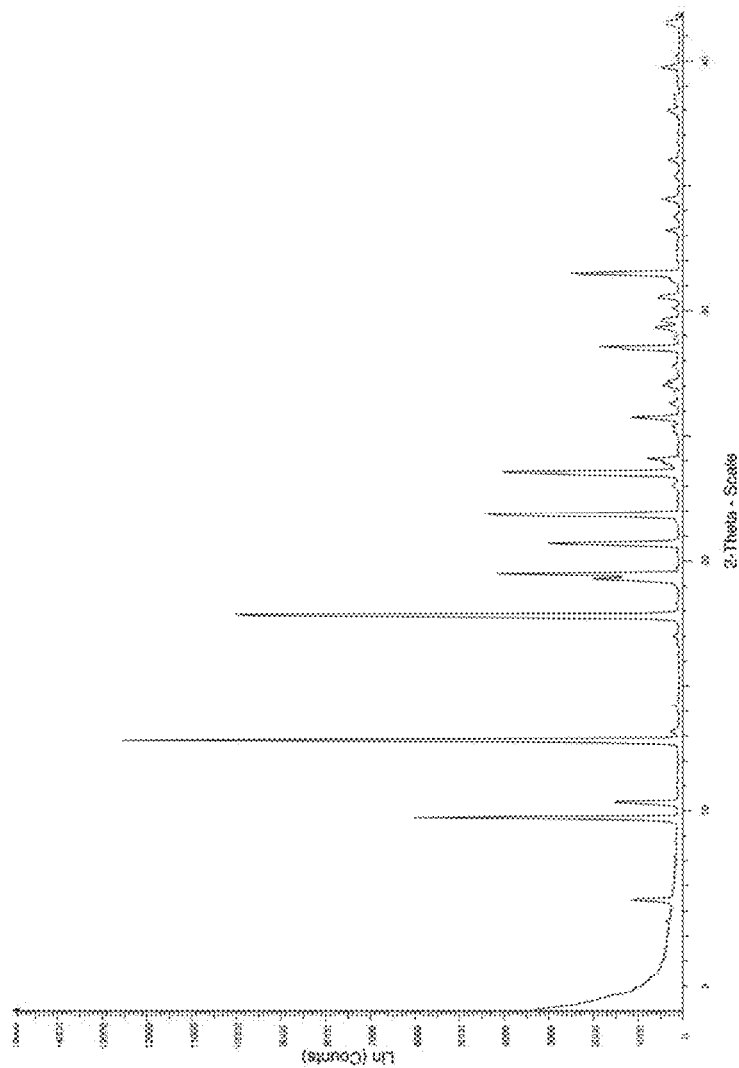
FIG. 26 shows the XRPD pattern for the 1:0.5 metaxalone maleic acid cocrystal.

The experimental XRPD pattern of the 1:0.5 metaxalone maleic acid cocrystal is shown in FIG. 26. Table 8 lists the angles, °2θ±0.2°2θ, d-spacing, and intensity of the peaks identified in the XRPD pattern of FIG. 26. The entire list of peaks, or a subset thereof, may be sufficient to characterize the cocrystal. One subset of peaks from FIG. 26 that, individually or in combination, may be used to characterize the 1:0.5 metaxalone maleic acid cocrystal includes 6.4, 9.7, 10.3, 12.8, 17.8, and 21.9 °2θ±0.2°2θ. The 1:0.5 metaxalone maleic acid cocrystal may be characterized by a subset of at least three of these peaks.

TABLE 8

| Angle °2θ ± 0.2° 2θ | d value Angstrom | Intensity % |
|---|---|---|
| 6.4 | 13.74 | 8.90 |
| 9.7 | 9.12 | 48.00 |
| 10.3 | 8.57 | 11.90 |
| 12.8 | 6.91 | 100.00 |
| 17.8 | 4.98 | 79.70 |
| 19.2 | 4.61 | 15.80 |
| 19.5 | 4.56 | 32.80 |
| 20.7 | 4.29 | 24.00 |
| 21.9 | 4.06 | 34.90 |
| 23.5 | 3.78 | 32.00 |
| 24.1 | 3.69 | 6.10 |
| 25.8 | 3.46 | 9.30 |
| 28.5 | 3.13 | 14.60 |
| 29.3 | 3.04 | 4.80 |
| 30.6 | 2.92 | 4.20 |
| 31.5 | 2.84 | 19.80 |

5.3 SCXRD Characterization of 1:0.5 Metaxalone Maleic Acid Cocrystal

The crystal used for single crystal structure determination was prepared as follows:

Ca. 500 mg of metaxalone was weighed into a glass vial followed by the addition of 0.5 equivalents of maleic acid. 1.67 ml of toluene was then added to the vial. The sample was subsequently matured for five days on a four hourly heat/cool cycle (50° C./RT). XRPD analysis of the sample showed that the cocrystal formation was incomplete. At this point the sample was split into two halves. To one half an additional 0.25 equivalents of acid was added together with 200 μl of toluene. The sample was then subjected to the same maturation cycle used previously for 1 further day. Re-analysis by XRPD showed that the cocrystal formation had now gone to completion but that there was also excess maleic acid present.

In order to filter the bulk sample, an additional aliquot of cold toluene, (200 μl) was added to the vial. The sample was then filtered under vacuum for ca. 30 minutes. After this time the sample was removed from the vacuum and stored at room temperature to dry for at least 16 hours.

Figure 27:
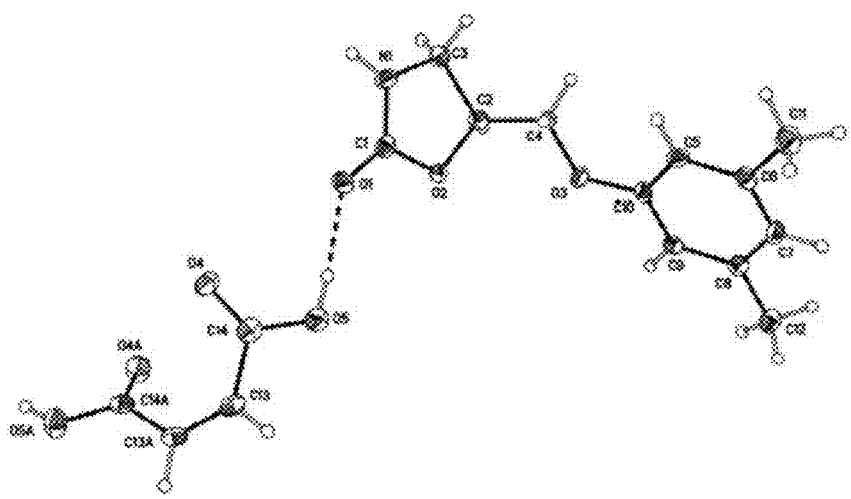
FIG. 27 shows an ORTEP drawing of the 1:0.5 metaxalone maleic acid cocrystal.
Figure 28:
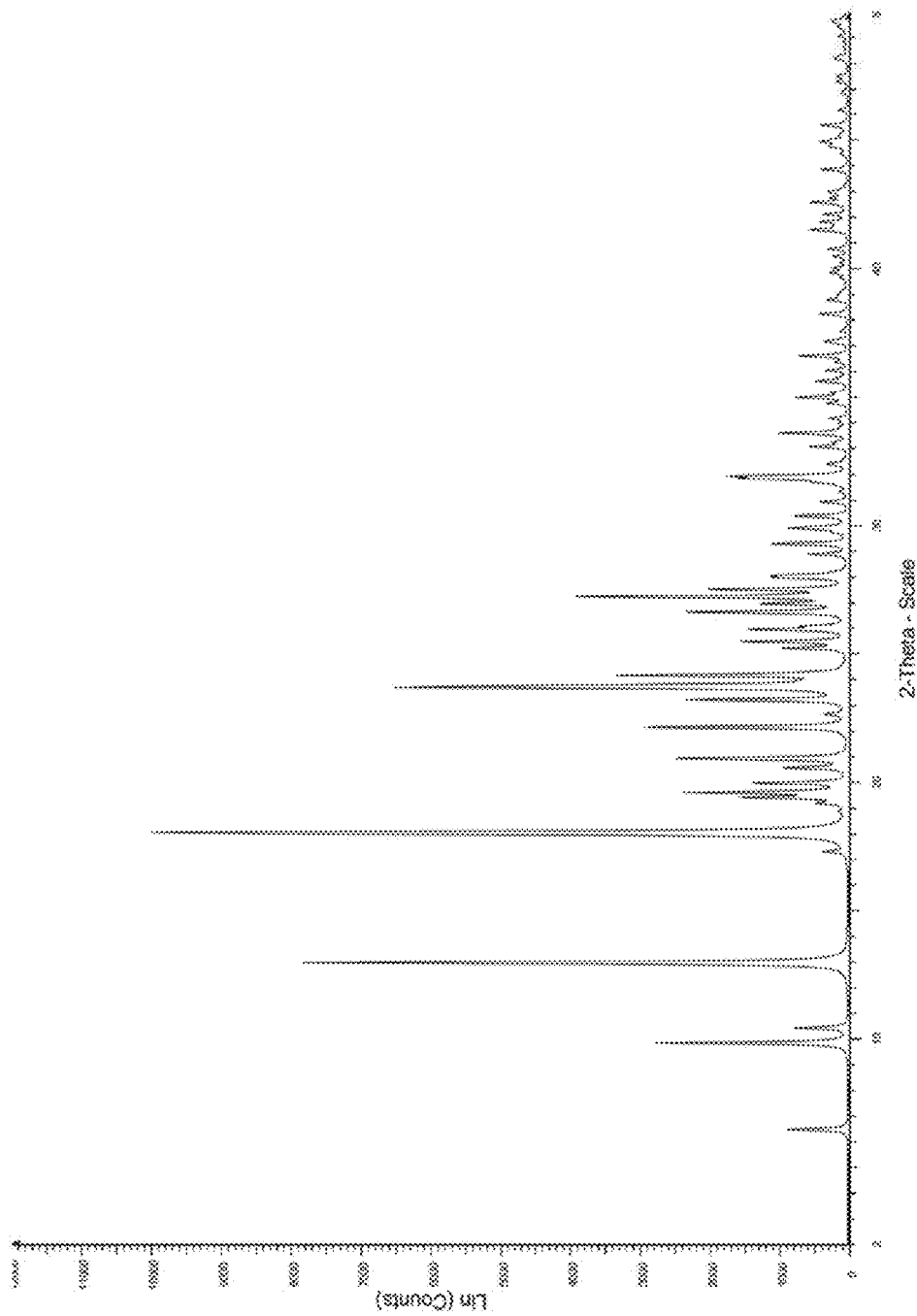
FIG. 28 shows a calculated XRPD pattern for the 1:0.5 metaxalone maleic acid cocrystal.

A suitable single crystal was isolated from the bulk dried material and determined by SCXRD analysis to be a 1:0.5 metaxalone maleic acid cocrystal. The single crystal data and structure refinement parameters are reported in Table 9. FIG. 27 shows an ORTEP drawing of the asymmetric unit from the crystal structure of the metaxalone maleic acid cocrystal showing the atom numbering scheme employed. Anisotropic atomic displacement ellipsoids for the non-hydrogen atoms are shown at the 50% probability level and hydrogen atoms are displayed as spheres of arbitrary radius. The calculated XRPD pattern based on the single crystal data and structure for the 1:0.5 metaxalone maleic acid cocrystal is shown in FIG. 28. It is also noted that there are some small temperature shifts in some of the peaks owing to the fact that the experimental XRPD pattern was collected at room temperature and the calculated XRPD pattern is derived from data collected at 120K. There are also small intensity differences owing to preferred orientation effects, present in the experimental pattern.

TABLE 9

| | |
|---|---|
| Molecular formula | $C_{14}H_{17}NO_5$ |
| Molecular weight | 279.29 |
| Crystal System | Monoclinic |
| Space Group | C2/c |
| Unit Cell Dimensions | a = 29.887(4) Å |
| | b = 5.3393(5) Å |
| | c = 18.523(3) Å |
| | α = 90.00° |
| | β = 113.481(16)° |
| | γ = 90.00° |
| Cell Volume | 2711.1(6) Å$^3$ |
| Z | 8 |
| Temperature | 120(1) K |
| Radiation Wavelength/type | 0.7107 Å/MoK\α |
| Goodness of fit | 1.006 |
| R factor | 0.0404 |
| Morphology | Colourless lath |

5.4 DSC of 1:0.5 Metaxalone Maleic Acid Cocrystal

Figure 29:
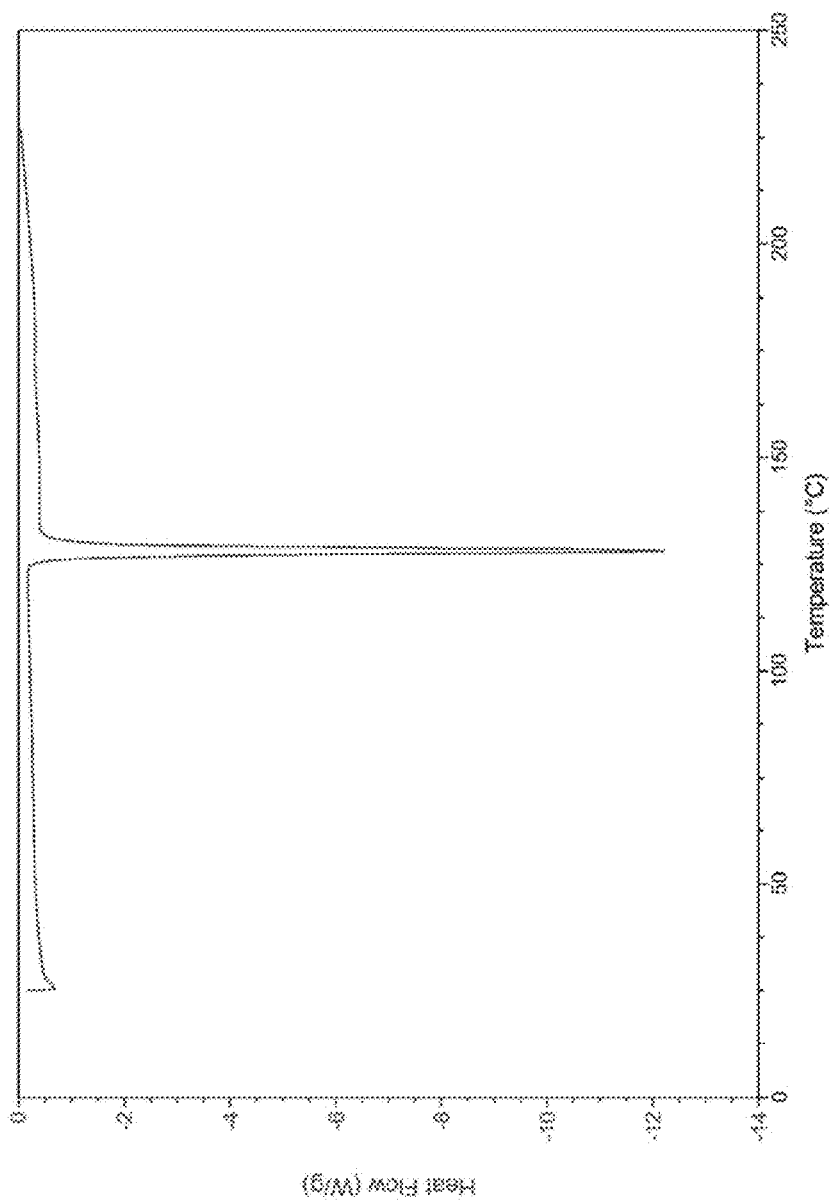
FIG. 29 shows the DSC trace for the 1:0.5 metaxalone maleic acid cocrystal.

The differential scanning calorimetry (DSC) trace, FIG. 29, shows a single endotherm with an onset temperature of 126.90 T and a peak maximum of 128.13° C.

5.5 TGA of 1:0.5 Metaxalone Maleic Acid Cocrystal

Figure 30:
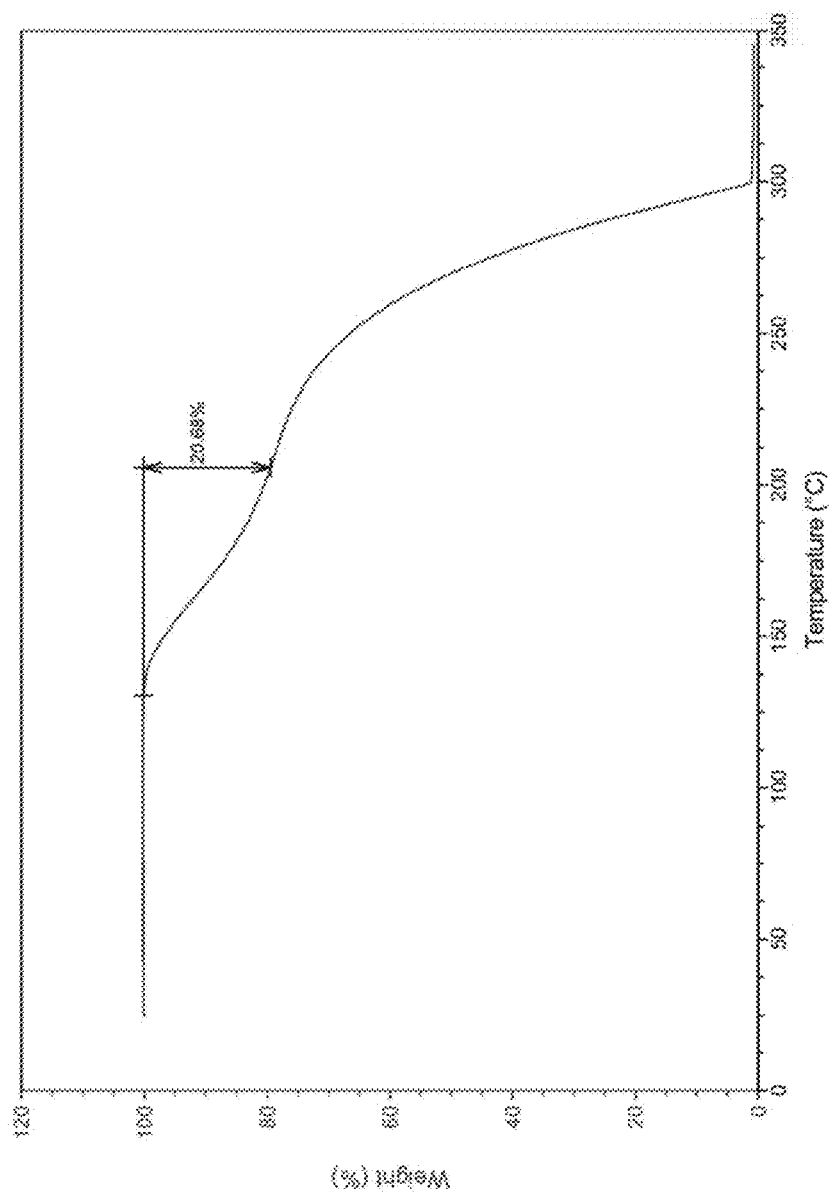
FIG. 30 shows the TGA trace for the 1:0.5 metaxalone maleic acid cocrystal.

In the thermal gravimetric analysis (TGA) trace, FIG. 30, it can be seen that after the cocrystal melt there is a 20.7% weight loss followed by apparent sublimation.

Figure 31:
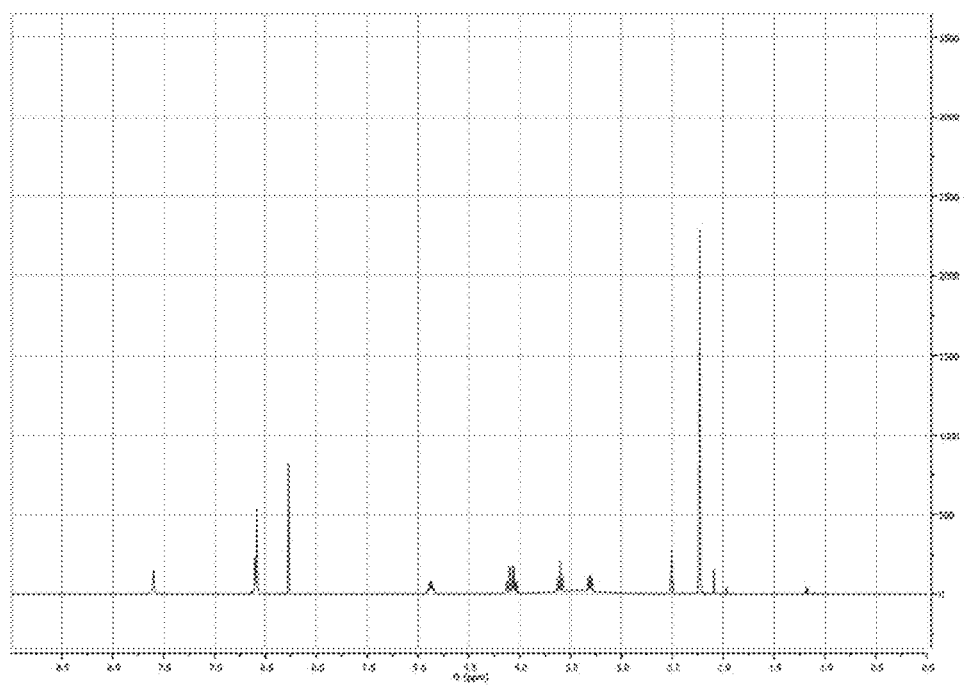
FIG. 31 shows the $^1$H NMR spectrum of the 1:0.5 metaxalone maleic acid cocrystal.

5.6 $^1$H NMR Spectrum of 1:0.5 Metaxalone Maleic Acid Cocrystal $^1$H spectrum of metaxalone maleic acid cocrystal, shown in FIG. 31, displays the following peaks: $^1$H NMR (400 MHz, d6-DMSO) δ: 7.60 (1H), 6.59 (3H), 6.27 (1H), 4.88 (1H), 4.07 (2H), 3.60 (1H), 3.32 (1H), 2.23 (6H). The peak at 6.27 ppm in the $^1$H NMR spectrum corresponds to the two protons on the double bond of maleic acid. Comparison of the integration of this peak with that at 4.88, which corresponds to one CH proton on the oxazolidinone ring of metaxalone, indicates that the cocrystal has a metaxalone:coformer stoichiometry of 1:0.5.

Example 6

Pharmacokinetic Study 6.1 Study Design

The study was designed to compare the pharmacokinetic profiles of the 1:0.5 metaxalone fumaric acid (prepared as described in Example 2.7) and 1:0.5 metaxalone succinic acid cocrystals (prepared as described in Example 4.7) with that of the crystalline metaxalone following oral administration under fasted conditions at 21 mg/kg dose level in beagle dogs. A crossover study was carried out using 5 male beagle dogs with a washout period of 5 days between each treatment. Prior to dosing, the dogs were fasted overnight, weighed and then this weight was used to load capsules with each test compound at an equivalent metaxalone dosage of 21 mg/kg. The capsules were orally administered to the dogs followed by about 10 mL of water. Food was provided 4 hours post-dose to all animals.

6.2 Blood Sample Collection

Blood samples were collected at pre-dose, 10, 20 and 30 minutes, and 1, 2, 3, 4, 6, 8, 12 and 24 hour post-dose (12 time points) following oral dose administration. Approximately 0.8 ml of whole blood was withdrawn from the cephalic vein and placed in labelled tubes containing $K_2$ EDTA as anticoagulant (20␣l of 200 mM $K_2$ EDTA solution per mL of blood). Plasma was separated by centrifuging the whole blood at about 2500 g for 10 minutes at 4° C. Separated plasma was stored below −70° C. until analysis.

6.3 Bioanalysis

A fit for purpose LC-MS/MS method was used for the determination of the metaxalone concentrations in the plasma samples. Pharmacokinetic parameters from individual samples were calculated using the non-compartmental analysis tool of the WinNonlin® software (version 5.2). The area under the plasma concentration curve (AUC) was calculated using the linear trapezoidal rule. Peak plasma concentration ($C_{max}$) and the time taken to reach the peak plasma concentration ($T_{max}$) were the observed values.

6.4 Pharmacokinetic Results

Figure 32:
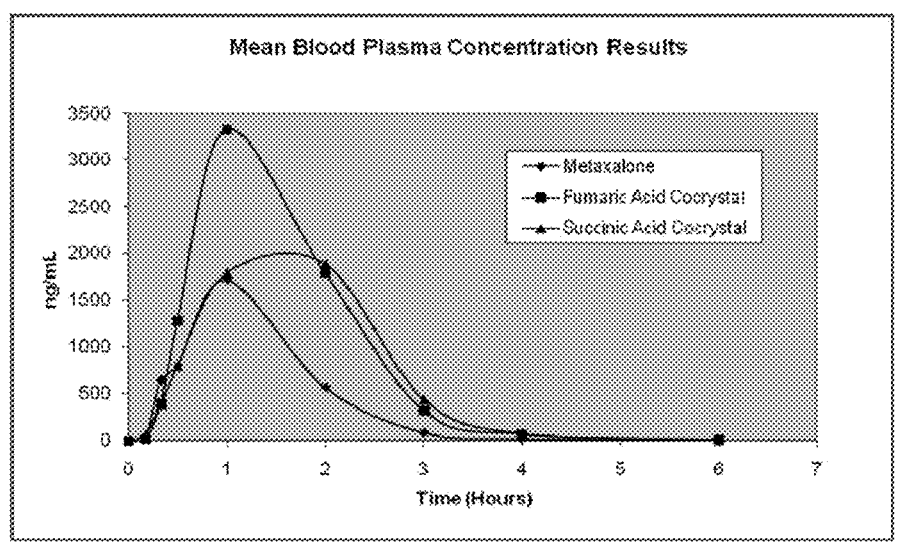
FIG. 32 shows the mean blood plasma concentration-time profiles from the pharmacokinetic study of Example 6.

The mean pharmacokinetic parameters for each sample are shown in Table 10. The mean blood plasma concentration-time profiles for all three test samples are shown in FIG. 32.

TABLE 10

| Test Item | $C_{max}$ (ng/mL) | $T_{max}$ (h) | AUC (ng · h/mL) |
|---|---|---|---|
| 1:0.5 Metaxalone Fumaric Acid Cocrystal | 3635.39 | 1.1 | 5202.44 |
| 1:0.5 Metaxalone Succinic Acid Cocrystal | 2629.8 | 1.8 | 4134.85 |
| Metaxalone | 1912.64 | 0.9 | 2377.29 |

The claimed invention is:

1. A metaxalone cocrystal selected from a 1:1 metaxalone adipic acid cocrystal, a 1:0.5 metaxalone fumaric acid cocrystal, a 1:1 metaxalone salicylic acid cocrystal, a 1:0.5 metaxalone succinic acid cocrystal, and a 1:0.5 metaxalone maleic acid cocrystal.

2. A metaxalone cocrystal of claim 1, wherein the cocrystal is a 1:1 metaxalone adipic acid cocrystal characterized by a powder X-ray diffraction pattern having at least three peaks selected from 8.5, 15.8, 18.9, 20.2, and 23.6 °2θ±0.2°2θ.

3. A metaxalone cocrystal of claim 1, wherein the cocrystal is a 1:1 metaxalone adipic acid cocrystal characterized by a powder X-ray diffraction pattern having peaks selected from 8.5, 15.8, 18.9, 20.2, and 23.6 °2θ±0.2°2θ, or by a powder X-ray diffraction pattern substantially similar to FIG. 1.

4. A metaxalone cocrystal of claim 1, wherein the cocrystal is a 1:0.5 metaxalone fumaric acid cocrystal characterized by a powder X-ray diffraction pattern having at least three peaks selected from 5.6, 11.0, 13.1, 18.3, 21.6, and 22.7 °2θ±0.2°2θ.

5. A metaxalone cocrystal of claim 1, wherein the cocrystal is a 1:0.5 metaxalone fumaric acid cocrystal characterized by a powder X-ray diffraction pattern having peaks selected from 5.6, 11.0, 13.1, 18.3, 21.6, and 22.7 °2θ±0.2°2θ, or by a powder X-ray diffraction pattern substantially similar to FIG. 5.

6. A metaxalone cocrystal of claim 1, wherein the cocrystal is a 1:1 metaxalone salicylic acid cocrystal characterized by a powder X-ray diffraction pattern having at least three peaks selected from 6.8, 16.1, 17.2, 22.6, and 24.6 °2θ±0.2°2θ.

7. A metaxalone cocrystal of claim 1, wherein the cocrystal is a 1:1 metaxalone salicylic acid cocrystal characterized by a powder X-ray diffraction pattern having peaks selected from 6.8, 16.1, 17.2, 22.6, and 24.6 °2θ±0.2°2θ, or by a powder X-ray diffraction pattern substantially similar to FIG. 12.

8. A metaxalone cocrystal of claim 1, wherein the cocrystal is a 1:0.5 metaxalone succinic acid cocrystal characterized by a powder X-ray diffraction pattern having at least three peaks selected from 6.4, 9.7, 10.2, 12.7, 20.6, and 21.7 °2θ±0.2°2θ.

9. A metaxalone cocrystal of claim 1, wherein the cocrystal is a 1:0.5 metaxalone succinic acid cocrystal characterized by a powder X-ray diffraction pattern having peaks selected from 6.4, 9.7, 10.2, 12.7, 20.6, and 21.7 °2θ±0.2°2θ, or by a powder X-ray diffraction pattern substantially similar to FIG. 19.

10. A metaxalone cocrystal of claim 1, wherein the cocrystal is a 1:0.5 metaxalone maleic acid cocrystal characterized by a powder X-ray diffraction pattern having at least three peaks selected from 6.4, 9.7, 10.3, 12.8, 17.8, and 21.9 °2θ±0.2°2θ.

11. A metaxalone cocrystal of claim 1, wherein the cocrystal is a 1:0.5 metaxalone maleic acid cocrystal characterized by a powder X-ray diffraction pattern having peaks selected from 6.4, 9.7, 10.3, 12.8, 17.8, and 21.9 °2θ±0.2°2θ, or by a powder X-ray diffraction pattern substantially similar to FIG. 26.

12. A pharmaceutical composition comprising at least one metaxalone cocrystal of claim 1 and a pharmaceutically acceptable carrier.

13. A method of treating a musculoskeletal condition comprising the step of administering to a patient in need thereof a therapeutically effective amount of at least one metaxalone cocrystal of claim 1.

14. A method of treating a musculoskeletal condition comprising the step of administering to a patient in need thereof a therapeutically effective amount of a pharmaceutical composition of claim 12.

15. A pharmaceutical composition comprising a metaxalone cocrystal of claim 3 and a pharmaceutically acceptable carrier.

16. A method of treating a musculoskeletal condition comprising the step of administering to a patient in need thereof a therapeutically effective amount of a metaxalone cocrystal of claim 3.

17. A pharmaceutical composition comprising a metaxalone cocrystal of claim 5 and a pharmaceutically acceptable carrier.

18. A method of treating a musculoskeletal condition comprising the step of administering to a patient in need thereof a therapeutically effective amount of a metaxalone cocrystal of claim 5.

19. A pharmaceutical composition comprising a metaxalone cocrystal of claim 7 and a pharmaceutically acceptable carrier.

20. A method of treating a musculoskeletal condition comprising the step of administering to a patient in need thereof a therapeutically effective amount of a metaxalone cocrystal of claim 7.

21. A pharmaceutical composition comprising a metaxalone cocrystal of claim 9 and a pharmaceutically acceptable carrier.

22. A method of treating a musculoskeletal condition comprising the step of administering to a patient in need thereof a therapeutically effective amount of a metaxalone cocrystal of claim 9.

23. A pharmaceutical composition comprising a metaxalone cocrystal of claim 11 and a pharmaceutically acceptable carrier.

24. A method of treating a musculoskeletal condition comprising the step of administering to a patient in need thereof a therapeutically effective amount of a metaxalone cocrystal of claim 11.

\* \* \* \* \*